United States Patent
Ishii et al.

(10) Patent No.: US 11,691,136 B2
(45) Date of Patent: Jul. 4, 2023

(54) OLEFIN OLIGOMERIZATION CATALYST AND METHOD FOR PRODUCING OLEFIN OLIGOMER IN THE PRESENCE OF THE SAME CATALYST

(71) Applicant: MITSUI CHEMICALS, INC., Tokyo (JP)

(72) Inventors: Seiichi Ishii, Ichihara (JP); Shinichiro Ichikawa, Chiba (JP); Terunori Fujita, Yokohama (JP)

(73) Assignee: MITSUI CHEMICALS, INC., Tokyo (JP)

( * ) Notice: Subject to any disclaimer, the term of this patent is extended or adjusted under 35 U.S.C. 154(b) by 331 days.

(21) Appl. No.: 16/628,144

(22) PCT Filed: Jul. 6, 2018

(86) PCT No.: PCT/JP2018/025626
§ 371 (c)(1),
(2) Date: Jan. 2, 2020

(87) PCT Pub. No.: WO2019/009390
PCT Pub. Date: Jan. 10, 2019

(65) Prior Publication Data
US 2020/0222886 A1 Jul. 16, 2020

(30) Foreign Application Priority Data

Jul. 6, 2017 (JP) .................................. 2017-132485
Jul. 6, 2017 (JP) .................................. 2017-132486

(51) Int. Cl.
| | | |
|---|---|---|
| B01J 31/34 | (2006.01) | |
| B01J 31/02 | (2006.01) | |
| B01J 31/14 | (2006.01) | |
| C07C 2/08 | (2006.01) | |
| C07C 11/04 | (2006.01) | |

(52) U.S. Cl.
CPC ........... B01J 31/34 (2013.01); B01J 31/0244 (2013.01); B01J 31/143 (2013.01); C07C 2/08 (2013.01); B01J 2231/20 (2013.01); C07C 11/04 (2013.01)

(58) Field of Classification Search
CPC ...... B01J 31/34; B01J 31/0244; B01J 31/143; B01J 2231/20; B01J 2531/62; B01J 31/1805; B01J 31/182; C07C 2/08; C07C 11/04; C07C 2531/18; C07C 2531/14; C07C 2/32; C07C 11/02; C07B 61/00
See application file for complete search history.

(56) References Cited

U.S. PATENT DOCUMENTS

| | | |
|---|---|---|
| 4,668,838 A | 5/1987 | Briggs |
| 4,990,640 A | 2/1991 | Tsutsui et al. |
| 5,321,106 A | 6/1994 | LaPointe |
| 6,121,393 A | 9/2000 | Kioka et al. |
| 6,844,290 B1 | 1/2005 | Maas et al. |
| 2006/0229480 A1 | 10/2006 | Blann et al. |
| 2010/0145124 A1 | 6/2010 | Han et al. |
| 2011/0082325 A1 | 4/2011 | Suzuki et al. |
| 2015/0045603 A1 | 2/2015 | Han et al. |
| 2016/0001278 A1 | 1/2016 | Saito et al. |
| 2017/0312738 A1* | 11/2017 | Lee ........................... C07F 9/46 |
| 2018/0071725 A1* | 3/2018 | Klosin ................ C07F 9/65685 |

FOREIGN PATENT DOCUMENTS

| | | |
|---|---|---|
| CN | 1045712 A | 10/1990 |
| EP | 0 237 079 A1 | 9/1987 |
| EP | 0 237 079 B1 | 9/1987 |
| EP | 0 426 637 A2 | 5/1991 |
| EP | 0 426 638 A2 | 5/1991 |
| EP | 0 427 696 A2 | 5/1991 |
| EP | 0 427 697 A2 | 5/1991 |
| EP | 2 899 196 A1 | 7/2015 |
| EP | 2 918 340 A1 | 9/2015 |
| EP | 2 987 783 A1 | 2/2016 |
| EP | 3 045 463 A1 | 7/2016 |
| EP | 3 101 039 A1 | 12/2016 |
| JP | S62-265237 A | 11/1987 |
| JP | S63-199703 A | 8/1988 |
| JP | H01-501950 A | 7/1989 |
| JP | H01-502036 A | 7/1989 |

(Continued)

OTHER PUBLICATIONS

Ruther et al., "Novel Chromium(III) Complexes Containing Imidazole-Based Chelate Ligands with Varying Donor Sets: Synthesis and Reactivity", Organometallics 2001, 20, 1247-1250. (Year: 2001).*

(Continued)

Primary Examiner — Ali Z Fadhel
(74) Attorney, Agent, or Firm — Foley & Lardner LLP

(57) ABSTRACT

A method for producing an olefin oligomer is disclosed, in which an olefin oligomerization reaction is performed in the presence of an olefin oligomerization catalyst comprising (A) a chromium compound, (B) an amine compound of the general formula (1):

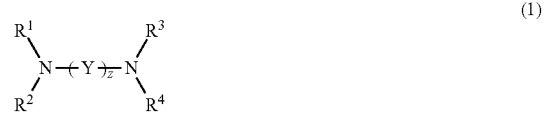

($R^1$ to $R^4$ represent a group such as a hydrocarbon group, Y represents a structure represented by $-CR^5R^6-$, $R^5$ and $R^6$ represent a group such as a hydrogen atom, and Z represents an integer of 1 to 10), and (C) a compound such as an organometal compound; and the olefin oligomerization catalyst.

12 Claims, No Drawings

(56) References Cited

FOREIGN PATENT DOCUMENTS

| JP | H02-78687 | A |   | 3/1990 |
|----|-----------|---|---|--------|
| JP | H03-179005 | A |   | 8/1991 |
| JP | H03-179006 | A |   | 8/1991 |
| JP | H03-207703 | A |   | 9/1991 |
| JP | H03-207704 | A |   | 9/1991 |
| JP | 2002-241419 | A |   | 8/2002 |
| JP | 2002241419 | A | * | 8/2002 |
| JP | 2016-203173 | A |   | 12/2016 |
| JP | 2017-095359 | A |   | 6/2017 |
| WO | WO-88/05792 | A1 |   | 8/1988 |
| WO | WO-88/05793 | A1 |   | 8/1988 |
| WO | WO-2004/056479 | A1 |   | 7/2004 |
| WO | WO-2009/005003 | A1 |   | 1/2009 |
| WO | WO-2009/022770 | A1 |   | 2/2009 |
| WO | WO-2013/137676 | A1 |   | 9/2013 |
| WO | WO-2016/093548 | A1 |   | 6/2016 |

OTHER PUBLICATIONS

McGuiness et al., "Ethylene Oligomerization with Cr-NHC Catalysts: Further Insights into the Extended Metallacycle Mechanism of Chain Growth", Organometallics 2008, 27, 4238-4247. (Year: 2008).*

European Extended Search Report, dated Mar. 2, 2021, issued in corresponding European Patent Application No. 18828440.0, (12 pages).

Tomov, et al, "Alternating [alpha]-Olefin Distributions via Single and Double Insertions in Chromium-Catalyzed Ethylene Oligomerization", Organometallics, [Online] 36(3): 510-522 (2016).

International Searching Authority, "International Search Report," issued in connection with International Patent Application No. PCT/JP2018/025626, dated Sep. 11, 2018.

International Searching Authority, "Written Opinion," issued in connection with International Patent Application No. PCT/JP2018/025626, dated Sep. 11, 2018.

* cited by examiner

OLEFIN OLIGOMERIZATION CATALYST AND METHOD FOR PRODUCING OLEFIN OLIGOMER IN THE PRESENCE OF THE SAME CATALYST

CROSS-REFERENCE TO RELATED APPLICATIONS

The present application claims priority under 37 U.S.C. § 371 to International Patent Application No. PCT/JP2018/025626, filed Jul. 6, 2018, which claims priority to and the benefit of Japanese Patent Application Nos. 2017-132485 and 2017-132486, both filed on Jul. 6, 2017. The contents of these applications are hereby incorporated by reference in their entireties.

TECHNICAL FIELD

The present invention relates to an olefin oligomerization catalyst having an excellent activity and providing a high selectivity and/or a production efficiency for a specific olefin oligomer, and a method of producing an olefin oligomer in the presence of the olefin oligomerization catalyst.

BACKGROUND ART

α-Olefins are important compounds widely used industrially, for example, as raw materials for polyolefins. For example, 1-hexene and 1-octene are highly demanded as raw materials for polyolefins. The α-olefin production methods that have been industrialized include a method using organoaluminum or a transition metal compound as a catalyst. However, in the industrialized methods, a mixture of many kinds of α-olefins is usually obtained. For this reason, it becomes difficult to flexibly conduct a business by responding to changes in the market conditions of each component, in some cases. Therefore, a production method having high selectivity for the intended α-olefin is desired.

Recent years, the present inventors have reported catalysts that enabled selective production of 1-hexene by ethylene trimerization reaction using transition metal complex compounds having phenoxyimine ligands (for example, Patent Document 1).

Further, chromium-based catalysts with phosphorus atom-containing ligands have been disclosed, for selective production of 1-octene (for example, Patent Documents 2 to 4).

PRIOR ART DOCUMENT

Patent Document

[Patent Document 1] WO 2009/005003
[Patent Document 2] WO 2004/056479
[Patent Document 3] WO 2013/137676
[Patent Document 4] WO 2009/022770

SUMMARY OF THE INVENTION

Problem to be Solved by the Invention

According to the investigations of the present inventors, since the performance relating one or more properties selected from the activity for reaction, the thermal stability and the selectivity of the α-olefin production was considered to be not sufficient in the conventional catalysts, further improvements have been desired.

In particular, when the conventional catalysts for selective production of 1-hexene were used, it was likely in many cases that selectivity of 1-octene was lower as compared with selectivity of 1-hexene, or 1-octene could not be obtained at all.

1-Octene is important as a raw material component for polyolefin production like 1-hexene, and especially important in case of the production of a high-performance polyolefin. Further, there is possibility that 1-octene becomes important as a raw material for lubricant.

The present invention has been made in view of the above problems. Thus, the present invention has an object of providing an olefin oligomerization catalyst having an excellent activity, particularly providing a high selectivity and/or a high production efficiency of 1-octene, and a method for producing an olefin oligomer in the presence of the olefin oligomerization catalyst.

Means for Solving the Problem

The present inventors have intensively studied to solve the above-described problems and resultantly found that a catalyst containing a specific transition metal compound, an amine compound having a specific structure and a cocatalyst has excellently high activity and/or high 1-octene selectivity. They have found that, in the presence of this catalyst, an olefin oligomerization reaction could be preferably conducted and that, in a particular case, 1-octene as a tetramer of ethylene could be obtained with a high activity, when ethylene is used as the olefin. Thus, the present inventors have completed the present invention.

The present invention can be specified by the following matters:

[1] A method for producing an olefin oligomer, comprising performing an olefin oligomerization reaction in the presence of an olefin oligomerization catalyst containing the following components (A) to (C):

(A) a chromium compound, (B) an amine compound represented by the following general formula (1):

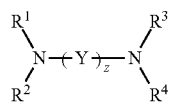

(1)

[In the general formula (1), $R^1$ to $R^4$ may be the same or different from each other, and each represents a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and two or more thereof may be connected each other.

Y represents a carbon atom having substituents $R^5$ and $R^6$ (a structure represented by $-CR^5R^6-$). $R^5$ and $R^6$ may be the same or different from each other, and each represents a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and $R^5$ and $R^6$ may be connected each other, and each of $R^5$ and $R^6$ may be connected to any one of $R^1$ to $R^4$.

Z represents an integer of 1 to 10], and (C) at least one compound selected from the group consisting of
- (C-1) an organometal compound,
- (C-2) an organoaluminumoxy compound and
- (C-3) a compound reacting with a transition metal compound to form an ion pair.

[2] The method for producing an olefin oligomer according to [1], wherein an amine compound (B) represented by the general formula (1) is used, in which $R^1$ is not connected to $R^3$ and $R^4$, and $R^2$ is not connected to $R^3$ and $R^4$.

[3] The method for producing an olefin oligomer according to [1], wherein an amine compound (B) represented by the general formula (1) is used, in which Z is an integer of 1 to 3.

[4] The method for producing an olefin oligomer according to [1], wherein an amine compound (B) represented by the general formula (1) is used, in which Z is 1.

[5] The method for producing an olefin oligomer according to [1], wherein an amine compound (B) represented by the general formula (1) is used, in which Z is an integer of 2 to 10.

[6] The method for producing an olefin oligomer according to [1], wherein the catalyst contains the following component (D) in addition to the components (A) to (C):

(D) a carrier for carrying at least one compound selected from the group consisting of the components (A) to (C).

[7] The method for producing an olefin oligomer according to [1], wherein the olefin oligomerization reaction is performed in the presence of an antistatic agent.

[8] The method for producing an olefin oligomer according to [1], wherein the olefin is ethylene.

[9] The method for producing an olefin oligomer according to [1], wherein the olefin oligomer is 1-octene.

[10] An olefin oligomerization catalyst comprising the following components (A) and (B):

(A) a chromium compound, and (B) an amine compound represented by the following general formula (1):

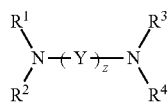

(1)

[In the general formula (1), $R^1$ to $R^4$ may be the same or different from each other, and each represents a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and two or more thereof may be connected each other.

Y represents a carbon atom having substituents $R^5$ and $R^6$ (a structure represented by $-CR^5R^6-$). $R^5$ and $R^6$ may be the same or different from each other, and each represents a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and $R^5$ and $R^6$ may be connected each other, and any of $R^5$ and $R^6$ may be connected to any one of $R^1$ to $R^4$.

Z represents an integer of 1 to 10].

[11] The olefin oligomerization catalyst according to [10], wherein Z is 1 in the general formula (1).

[12] The olefin oligomerization catalyst according to [10], wherein the component (A) is a trivalent chromium compound.

[13] The olefin oligomerization catalyst according to [10], comprising the following component (C) in addition to the components (A) and (B):

(C) at least one compound selected from the group consisting of
- (C-1) an organometal compound,
- (C-2) an organoaluminumoxy compound and
- (C-3) a compound reacting with a transition metal compound to form an ion pair.

Effect of the Invention

The present invention can provide an olefin oligomerization catalyst having excellent activity and particularly giving high selectivity and/or production efficiency of 1-octene, and a method for producing an olefin oligomer in the presence of the olefin oligomerization catalyst.

MODES FOR CARRYING OUT THE INVENTION

Embodiments of the present invention will be illustrated below, but the present invention is not limited to them. In the present invention, the olefin oligomerization means oligomer formation of a dimer to a decamer, preferably a trimer or a tetramer, from an olefin.

<Chromium Compound (A)>

The chromium compound (A) used in the present invention is usually an inorganic salt, an organic salt or a metal organic complex of chromium. Concrete examples of the chromium compound (A) include chromium (III) chloride, chromium (II) chloride, chromium (III) bromide, chromium (II) bromide, chromium (III) iodide, chromium (II) iodide, chromium (III) fluoride, chromium (II) fluoride, chromium trichloride tristetrahydrofuran, chromium (III) 2-ethyl-hexanoate, chromium(III) acetylacetonate, chromium (III) trifluoroacetylacetonate and chromium (III) hexafluoro-acetylacetonate. The chromium compound (A) is not limited to them. Regarding the above compounds, a trivalent chromium compound is preferable. A chromium compound containing a halogen atom is also preferable.

<Amine Compound (B)>

The amine compound (B) used in the present invention is represented by the following general formula (1):

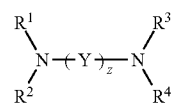

(1)

In the general formula (1), $R^1$ to $R^4$ may be the same or different from each other, and each represents a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and two or more thereof may be connected each other. More concretely, each of $R^1$ to $R^4$ represents preferably a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amide group, an imide group, an amino group, an imino group, a sulfoneester group, a sulfoneamide group, a cyano group, a nitro group, a carboxyl group, a sulfo group, a mercapto group, an aluminum-containing group or a hydroxy group.

When at least one of $R^1$ to $R^4$ is a halogen atom, concrete examples of the halogen atom include fluorine, chlorine, bromine and iodine.

When at least one of $R^1$ to $R^4$ is a hydrocarbon group, concrete examples of the hydrocarbon group include linear or branched alkyl groups having a number of carbon atoms of 1 to 30, preferably 1 to 20, more preferably 1 to 10, such as methyl, ethyl, n-propyl, isopropyl, n-butyl, isobutyl, sec-butyl, tert-butyl, neopentyl and n-hexyl; linear or branched alkenyl groups having a number of carbon atoms of 2 to 30, preferably 2 to 20, such as vinyl, allyl and isopropenyl; linear or branched alkynyl groups having a number of carbon atoms of 2 to 30, preferably 2 to 20, such as ethynyl and propargyl; cyclic saturated hydrocarbon groups having a number of carbon atoms of 3 to 30, preferably 3 to 20, such as cyclopropyl, cyclobutyl, cyclopentyl, cyclohexyl and adamantyl; cyclic unsaturated hydrocarbon groups having a number of carbon atoms of 5 to 30, such as cyclopentadienyl, indenyl and fluorenyl; aryl groups having a number of carbon atoms of 6 to 30, preferably 6 to 20, such as phenyl, naphthyl, biphenyl, terphenyl, phenanthryl and anthracenyl; alkyl-substituted aryl groups, such as tolyl, isopropylphenyl, tert-butylphenyl, dimethylphenyl and di-tert-butylphenyl; and alkylidene groups having a number of carbon atoms of 1 to 30, preferably 5 to 10, such as benzylidene, methylidene and ethylidene.

When at least one of $R^1$ to $R^4$ is a hydrocarbon group, a hydrogen atom(s) may be substituted with a halogen in the hydrocarbon group. Concrete examples thereof include halogenated hydrocarbon groups having a number of carbon atoms of 1 to 30, preferably 1 to 20 such as trifluoromethyl, pentafluorophenyl and chlorophenyl.

When at least one of $R^1$ to $R^4$ is a hydrocarbon group, a hydrogen atom(s) may be substituted with another hydrocarbon group in the hydrocarbon group. Concrete examples thereof include aryl group-substituted alkyl groups such as benzyl, cumyl, diphenylethyl and trityl.

When at least one of $R^1$ to $R^4$ is a hydrocarbon group, the hydrocarbon group may have additionally a heterocyclic compound residue; an oxygen-containing group such as an alkoxy group, an aryloxy group, an ester group, an ether group, an acyl group, a carboxyl group, a carbonate group, a hydroxy group, a peroxy group and a carboxylic anhydride group; a nitrogen-containing group such as an amino group, an imino group, an amide group, an imide group, a hydrazino group, a hydrazono group, a nitro group, a nitroso group, a cyano group, an isocyano group, a cyanate ester group, an amidino group, a diazo group and an amino group in the form of an ammonium salt; a boron-containing group such as a boranediyl group, a boranetriyl group and a diboranyl group; a sulfur-containing group such as a mercapto group, a thioester group, a dithioester group, an alkylthio group, an arylthio group, a thioacyl group, a thioether group, a thiocyanate group, an isothiocyanate group, a sulfonic acid ester group, a sulfoneamide group, a thiocarboxyl group, a dithiocarboxyl group, a sulfo group, a sulfonyl group, a sulfinyl group and a sulfenyl group; or a phosphorus-containing group such as a phosphide group, a phosphoryl group, a thiophosphoryl group and a phosphate group, a silicon-containing group, a germanium-containing group or a tin-containing group. Regarding these compounds, preferable examples include linear or branched alkyl groups having 1 to 30 carbon atoms, preferably 1 to 20 carbon atoms, more preferably 1 to 10 carbon atoms, particularly preferably 2 to 10 carbon atoms, such as methyl, ethyl, n-propyl, isopropyl, n-butyl, isobutyl, sec-butyl, tert-butyl, neopentyl, n-hexyl and adamantyl; aryl groups having 6 to 30 carbon atoms, preferably 6 to 20 carbon atoms, such as phenyl, naphthyl, biphenyl, terphenyl, phenanthryl and anthracenyl; and substituted aryl groups having 1 to 5 substituents, such as halogen atoms; alkyl groups and alkoxy groups both of which have 1 to 30 carbon atoms, preferably 1 to 20 carbon atoms; amino groups; aryl groups and aryloxy groups both of which have 6 to 30 carbon atoms, preferably 6 to 20 carbon atoms.

When at least one of $R^1$ to $R^4$ is an oxygen-containing group, a nitrogen-containing group, a sulfur-containing group and/or a phosphorus-containing group, concrete examples thereof include the groups as exemplified previously as the substituents which may be contained in the hydrocarbon group. Regarding these compounds, oxygen-containing groups, nitrogen-containing groups and sulfur-containing groups are preferable, and oxygen-containing groups and nitrogen-containing groups are more preferable.

As the above-described nitrogen-containing group, examples thereof include an amide group, an amino group, an imide group and an imino group. Concrete examples of the amide group include acetamide, N-methylacetamide and N-methylbenzamide. Concrete examples of the amino group include dimethylamino, ethylmethylamino and diphenylamino. Concrete examples of the imide group include acetoimide and benzimide. Concrete examples of the imino group include methylimino, ethylimino, propylimino, butylimino and phenylimino.

As the above-described sulfur-containing group, examples thereof include an alkylthio group, an arylthio group, a thioester group, a sulfonic acid ester group and a sulfoneamide group. Concrete examples of the alkylthio group include a methylthio group and an ethylthio group. Concrete examples of the arylthio group include a phenylthio group, a methylphenylthio group and a naphthylthio group. Concrete examples of the thioester group include an acetylthio group, a benzoylthio group, a methylthiocarbonyl group and a phenylthiocarbonyl group. Concrete examples of the sulfonic acid ester group include a methyl sulfonate group, an ethyl sulfonate group and a phenyl sulfonate group. Concrete examples of the sulfoneamide group include a phenylsulfoneamide group, N-methylsulfoneamide group and a N-methyl-p-toluenesulfoneamide group.

When at least one of $R^1$ to $R^4$ is a heterocyclic compound residue, concrete examples of the heterocyclic compound residue include residues from nitrogen-containing compounds such as pyrrole, pyridine, pyrimidine, quinoline and triazine, oxygen-containing compounds such as furan and pyran, and sulfur-containing compounds such as thiophene, The above residues may be further substituted on these heterocyclic compound residues, with a substituent(s) such as an alkyl group and an alkoxy group each of which has 1 to 30 carbon atoms, preferably 1 to 20 carbon atoms.

When at least one of $R^1$ to $R^4$ is a boron-containing group, concrete examples of the boron-containing group include the groups as exemplified previously as the substituents which may be contained in the hydrocarbon group. Additional examples include groups comprising alkyl group-substituted boron, aryl group-substituted boron, boron halide or alkyl group-substituted boron halide. Examples of the groups comprising alkyl group-substituted boron include, for example, $(Et)_2B—$, $(iPr)_2B—$, $(iBu)_2B—$, $(Et)_3B$, $(iPr)_3B$ and $(iBu)_3B$. Examples of the groups comprising aryl group-substituted boron include, for example, $(C_6H_5)_2B—$, $(C_6H_5)_3B$, $(C_6F_5)_3B$ and $(3,5-(CF_3)_2C_6H_3)_3B$. Examples of the groups comprising boron halide include, for example, $BCl_2—$ and $BCl_3$. Examples of the groups comprising alkyl group-substituted boron halide include, for example, $(Et)BCl—$, $(iBu)BCl—$ and $(C_6H_5)_2BCl$.

In the above formulae, Et represents an ethyl group, iPr represents an isopropyl group and iBu represents an isobutyl group. Further, tri-substituted boron may be in the form of coordination bond.

When at least one of $R^1$ to $R^4$ is an aluminum-containing group, concrete examples of the aluminum-containing group include groups of alkyl group-substituted aluminum, aryl group-substituted aluminum, halogenated aluminum and alkyl group-substituted halogenated aluminum. Examples of the groups comprising alkyl group-substituted aluminum include, for example, $(Et)_2Al—$, $(iPr)_2Al—$, $(iBu)_2Al—$, $(Et)_3Al$, $(iPr)_3Al$ and $(iBu)_3Al$. Examples of the groups comprising aryl group-substituted aluminum include, for example, $(C_6H_5)_2Al—$. Examples of the groups comprising halogenated aluminum include, for example, $AlCl_2—$ and $AlCl_3$. Examples of the groups comprising alkyl group-substituted halogenated aluminum include, for example, $(Et)AlCl—$ and $(iBu)AlCl—$. In the above formulae, Et represents an ethyl group, iPr represents an isopropyl group and iBu represents an isobutyl group. Further, tri-substituted aluminum may be in the form of coordination bond.

When at least one of $R^1$ to $R^4$ is a silicon-containing group, concrete examples of the silicon-containing group include a silyl group, a siloxy group, a hydrocarbon-substituted silyl group and a hydrocarbon-substituted siloxy group. The hydrocarbon-substituted silyl group includes, for example, methylsilyl, dimethylsilyl, trimethylsilyl, ethylsilyl, diethylsilyl, triethylsilyl, diphenylmethylsilyl, triphenylsilyl, dimethylphenylsilyl, dimethyl tert-butylsilyl and dimethyl(pentafluorophenyl)silyl. Regarding the above groups, preferable examples include methylsilyl, dimethylsilyl, trimethylsilyl, ethylsilyl, diethylsilyl, triethylsilyl, dimethylphenylsilyl and triphenylsilyl, and more preferable examples include trimethylsilyl, triethylsilyl, triphenylsilyl and dimethylphenylsilyl. Examples of the hydrocarbon-substituted siloxy group include trimethylsiloxy.

When at least one of $R^1$ to $R^4$ is a germanium-containing group and/or a tin-containing group, concrete examples thereof include the groups as obtained by substituting silicon of any silicon-containing groups as descried above with germanium or tin.

In the general formula (1), Y represents a carbon atom having substituents $R^5$ and $R^6$ (a structure represented by $—CR^5R^6—$). $R^5$ and $R^6$ may be the same or different from each other, and each represent a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and examples of these groups are the same as examples of $R^1$ to $R^4$. $R^5$ and $R^6$ may be connected each other, and any of $R^5$ and $R^6$ may be connected to any one of $R^1$ to $R^4$.

In the general formula (1), Z represents an integer of 1 to 10. Z may be preferably 2 to 10. Z is preferably an integer of 1 to 3, more preferably 1 or 2, particularly preferably 1. When Z is 2 or more, a plurality of Y may be the same or different from each other.

In the general formula (1), two or more of $R^1$ to $R^4$ may be connected each other. It is preferable that $R^1$ is not connected to both of $R^3$ and $R^4$, and $R^2$ is not connected to both of $R^3$ and $R^4$. The amine compound in which the specific group(s) having no connection as described above includes, for example, three types of amine compounds represented by the following general formulae (1A) to (1C):

(1A)

(in the general formula (1A), the definition of each group is the same as the definition of each group in the general formula (1). In this formula (1A), $R^1$ to $R^4$ are not connected each other.)

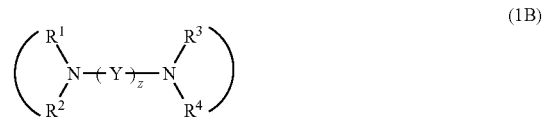
(1B)

(in the general formula (1B), the definition of each group is the same as the definition of each group in the general formula (1). In this formula (1B), $R^1$ and $R^2$ are connected each other, while $R^3$ and $R^4$ are connected each other.)

(1C)

(in the general formula (1C), the definition of each group is the same as the definition of each group in the general formula (1). In this formula (1C), each of $R^1$ and $R^2$ is not connected to the other groups regarding these four groups, while $R^3$ and $R^4$ are connected.)

In the general formula (1), $R^1$ to $R^4$ may be a linear or branched group or may be a group containing a ring structure, alternatively two or more of $R^1$ to $R^4$ may be connected each other to form a ring structure. For example, when $R^1$ and $R^3$ are connected (bonded) each other, or alternatively $R^2$ and $R^4$ are connected (bonded) each other, the number of bonds for each connection preferably 4 or more, and when not only $R^1$ and $R^3$, but also $R^2$ and $R^4$ are connected (bonded) each other, the number of bonds for each connection is preferably 3 or more. As represented by the general formulae (1A) to (1C), it is preferable not only that $R^1$ is not connected to both of $R^3$ and $R^4$, but also that $R^2$ is not connected to both of $R^3$ and $R^4$. It is preferable that each of $R^1$ to $R^4$ has no substituent having a ring structure, i. e., they are linear or branched groups. When $R^1$ to $R^4$ are linear or branched groups (for example, a linear or branched hydrocarbon group optionally having a substituent), the number of carbon atoms of the linear or branched group is preferably 3 to 20, more preferably 3 to 15, particularly preferably 3 to 10. In this case, the total number of carbon atoms of $R^1$ to $R^4$ is preferably 8 or more. All of $R^1$ to $R^4$ are preferably linear.

When $R^1$ to $R^4$ represent any of the above-described preferable groups, there is a tendency that the reaction activity of an olefin is higher, and that an α-olefin having relatively low boiling point such as from dimer to pentamer (preferably, from trimer to tetramer) can be easily produced more efficiently. When the raw material is ethylene, the trimer and the tetramer thereof correspond to hexene and octene, respectively. Thus, it tends to be suitable for production of an olefin having 10 or less carbon atoms.

When an olefin oligomerization catalyst containing an amine compound (B) of the present invention is used, the ratio of the amount of the above-described olefin oligomers, thus produced, i. e., from dimer to pentamer (preferably, from trimer to tetramer) tends to be higher, with respect to the total amount of all products thus produced Specifically, this ratio is desirably 85% or more by weight, preferably 88% or more by weight, more preferably 90% or more by weight, particularly preferably 91% or more by weight. When the ratio of the amount of, for example, from dimer to pentamer (preferably, from trimer to tetramer) thus produced is high as described above, the variety of the oligomers thus produced tends to be reduced. Further, since the boiling points of the components have relatively large differences, it becomes easy to separate them by distillation (for example, the boiling point of 1-hexene is 63° C., while the boiling point of 1-octene is 122 to 123° C.). As a result, it is considered that the production cost can be suppressed and it becomes easy to respond to the influence by the movement of the market condition.

In one aspect, both of $R^1$ and $R^2$ and/or both of $R^3$ and $R^4$ preferably have the same structure. In this case, the selection rate of a tetramer of ethylene, i. e., 1-octene, may become higher. Regarding the amine compounds (B), the amine compounds (B-1) and (B-11) meet the above case, for example, wherein all of $R^1$ to $R^4$ represent a methyl group as used in the examples described later.

When $R^1$ and $R^2$ are connected to form a ring structure, and/or when $R^3$ and $R^4$ are connected to form a ring structure, it is also preferable that $R^1$ and $R^2$ have the same structure and/or that $R^3$ and $R^4$ have the same structure. In this case, "the same structure" means that the ring structure is symmetric to "N" as the view point, i. e., the structure of the $R^1$ side part (or the $R^3$ side part) and the structure of the $R^2$ side part (or the $R^4$ side part) of the ring structure are the same. In this case, the selection rate of a tetramer of ethylene, i. e., 1-octene also may become higher. Among amine compounds (B), the amine compounds (B-2) and (B-10) used in the examples described later meet the above case, wherein the amine compounds (B-2) has $R^1$ and $R^2$ connected each other and $R^3$ and $R^4$ connected each other to form a 5-membered ring, respectively, and the amine compound (B-10) has $R^1$ and $R^2$ connected each other and $R^3$ and $R^4$ connected each other to form a 6-membered ring, respectively.

When $R^1$ and $R^2$ are connected and/or when $R^3$ and $R^4$ are connected, the number of carbon atoms of each of $R^1$ and $R^2$ (and/or the number of carbon atoms of each of $R^3$ and $R^4$) is defined by the carbon atom number of each part divided at the half point of the connection structure as the boundary thereof, in the present invention. For example, regarding amine compounds (B) used in the examples described later, the number of carbon atoms of each of $R^1$ to $R^4$ in the amine compound (B-4) is defined as 3, while, the number of carbon atoms of each of $R^1$ and $R^3$ is defined as 3.5 and the number of carbon atoms of each of $R^2$ and $R^4$ is defined as 2.5 in the amine compound (B-3).

It is indefinite why more excellent effects can be obtained when $R^1$ and $R^2$ have the same structure and/or when $R^3$ and $R^4$ have the same structure. Since $R^1$ to $R^4$ are considered to be located relatively close to the chromium atom of the central metal chromium compound (A), it is presumed that easiness of ethylene coordination into the metallacycle and activation energy of the insertion reaction are appropriately controlled, under the steric influence of $R^1$ to $R^4$ having the structure as described above.

In the present invention, one of the indicators for comprehensively judging the performance of an olefin oligomerization catalyst is the catalytic activity for 1-octene production described in the examples described later. The catalytic activity for 1-octene production can be defined as the amount of 1-octene production per unit time and unit amount of a catalyst, i. e., the production efficiency of 1-octene. This 1-octene production efficiency is different from the selection rate of 1-octene, as the indicator.

Further, the suitable embodiments described above are preferred, regarding not only the further improvement of the production efficiency of a trimer of ethylene (1-hexene) or a tetramer of ethylene (1-octene), but also the reaction activity of ethylene and efficient production of 1-octene.

When an oligomer of ethylene is produced in the present invention, 1-hexene and 1-octene can be main products. Separation thereof each other can be relatively easy by distillation. Therefore, the production efficiency of 1-octene described above is considered to be an important indicator from the industrial view point. Particularly, the catalytic activity can be an important indicator, when a production equipment for co-production of 1-hexene and 1-octene is used.

Concrete examples of the amine compound (B) are shown below, but the amine compound (B) is not limited to them.

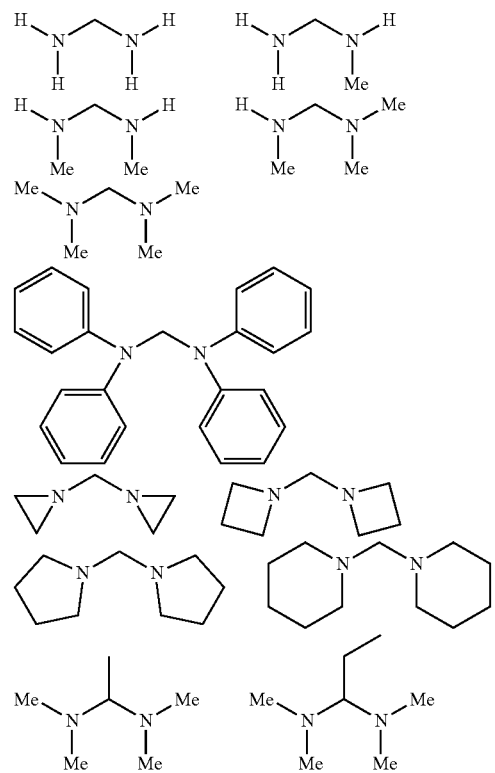

-continued
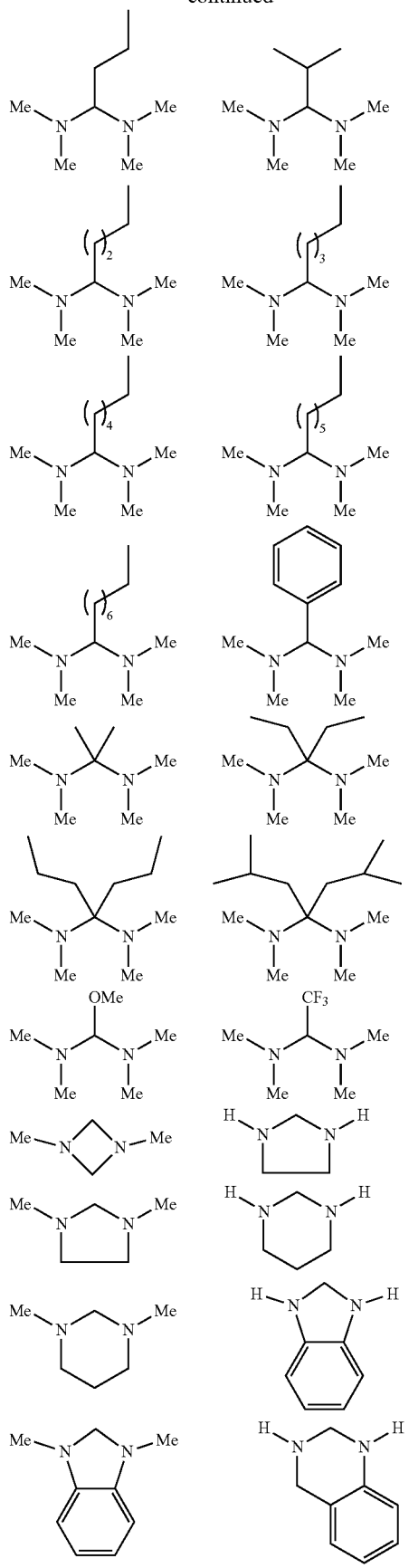
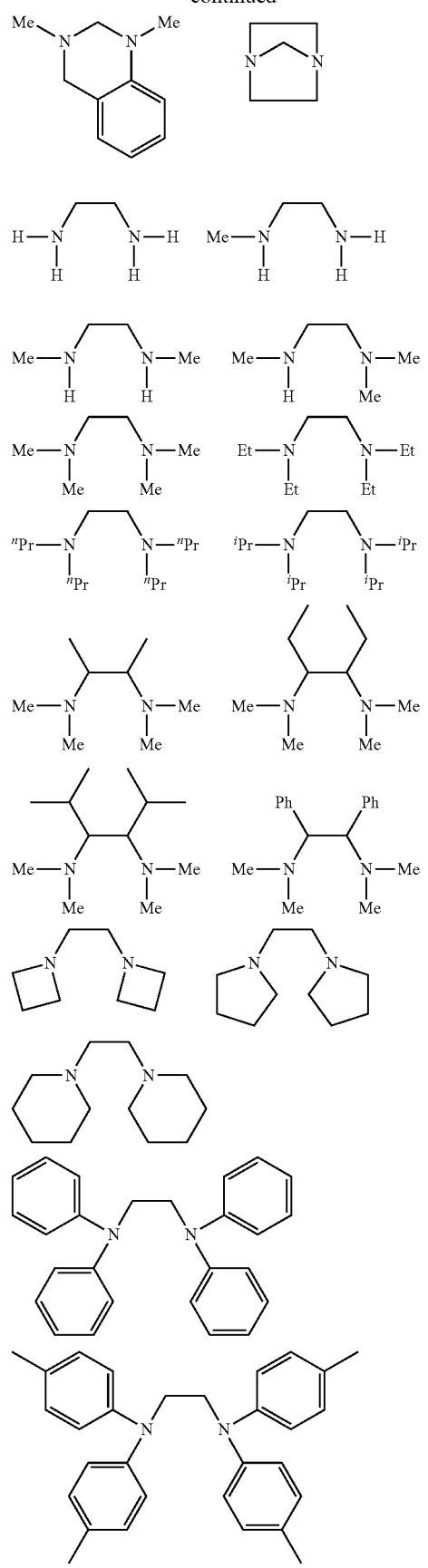

-continued

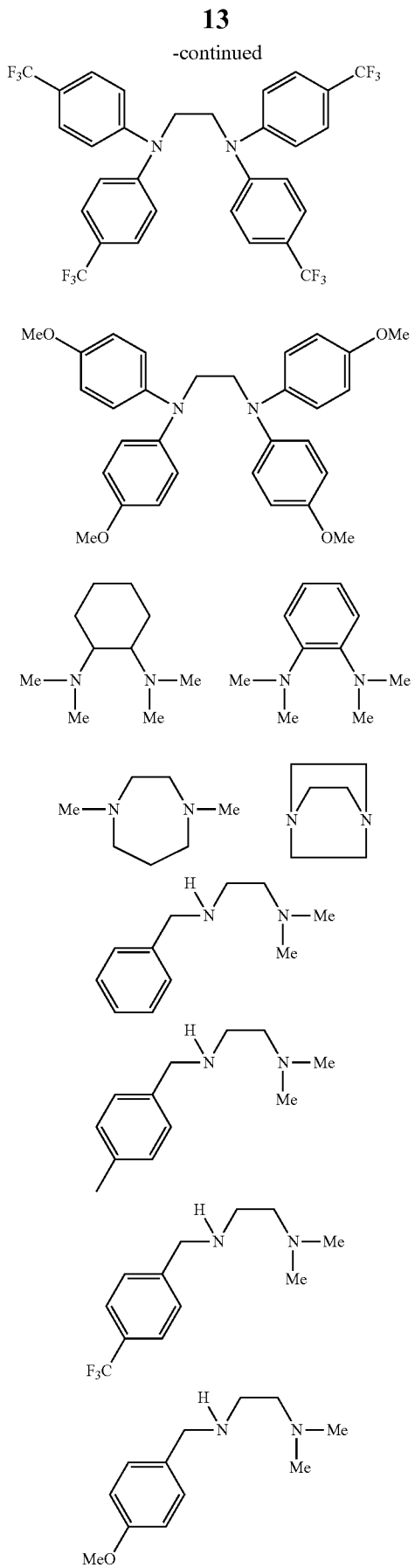

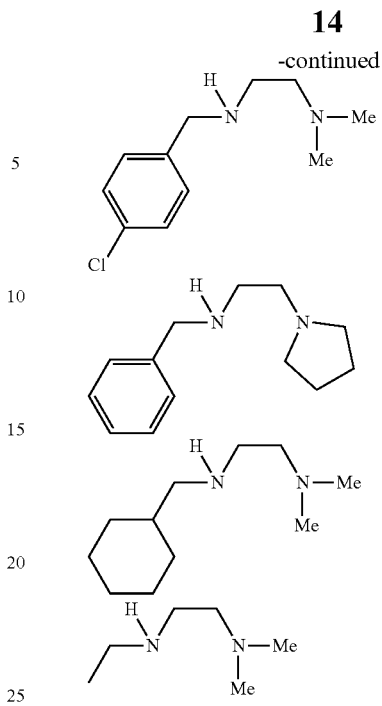

Regarding each of the above-described compounds, Me represents a methyl group, Et represents an ethyl group, nPr represents a n-propyl group, iPr represents an isopropyl group and Ph represents a phenyl group. The compounds, which can be obtained by changing the carbon atom number of 1 or 2 between N and N in the above-described compounds to 3 can be also used.

As the amine compound (B), commercially available amine compounds may be used. In the case of synthesis of an amine compound (B), for example, an amine compound (B) can be obtained by alkylating or arylating a specific amine compound by a conventional method. An amine compound (B) can be also obtained by reducing an imine compound by a conventional method. Further, in the present invention, two or more amine compounds (B) can be also used in combination.

When an olefin oligomerization catalyst containing an amine compound (B) of the present invention is used, there is a tendency that 1-octene can be produced efficiently as described above. For example, the ratio of 1-octene is desirably 40% or more by weight, preferably 50% or more by weight, more preferably 60% or more by weight, particularly preferably 65% or more by weight, most preferably 70% or more by weight, in the olefin oligomers having 10 or less carbon atoms thus produced.

An amine compound (B) and a chromium compound (A) may be separately added to a reaction vessel. However, it is preferable that a transition metal complex previously formed by reacting an amine compound (B) and a chromium compound (A) is added to a reaction vessel. For example, a transition metal complex can be obtained by dissolving an amine compound (B) in a solvent, mixing the resultant solution with a chromium compound (A), and stirring the resultant mixture for about 5 minutes to 48 hours under an inert gas atmosphere such as nitrogen or argon, at −78° C. to room temperature or under reflux conditions.

The solvent used in synthesizing a transition metal complex is not particularly restricted. Commonly known and usable solvents in such a reaction can be used. Concrete examples of the solvent include polar solvents such as ether and tetrahydrofuran; hydrocarbon solvents such as toluene, methylcyclohexane and heptane; and halogenated hydrocarbon solvents such as methylene chloride, i. e., dichloromethane.

The transition metal complex may be obtained in a dissolved state or a suspended state in a solvent. The transition metal complex solution or suspension may be used as it is, or the transition metal complex may be isolated once and again dissolved or suspended in a solvent before use.

<Compound (C)>

The compound (C) used in the present invention is at least one compound selected from the group consisting of an organometal compound (C-1), an organoaluminumoxy compound (C-2) and a compound (C-3) in order to form an ion pair by reaction with a transition metal compound. These compounds (C-1) to (C-3) will be described below. In the following descriptions, the compound (C-3) is described as "ionized ionic compound (C-3)".

[Organometal Compound (C-1)]

As the organometal compound (C-1), for example, organometal compounds can be used, which have metallic atoms belonging to the periodic table Groups 1, 2, 12 and 13, such as the compounds (C-1a), (C-1b) and (C-1c) described below.

According to the present invention, the organoaluminumoxy compound (C-2) described later is excluded from the organometal compound (C-1).

(C-1a): Organoaluminum compounds represented by the general formula $R^a_m Al(OR^b)_n H_p X_q$ (wherein, $R^a$ and $R^b$ may be the same or different from each other and each represents a hydrocarbon group having 1 to 15 carbon atoms, preferably 1 to 4 carbon atoms, X represents a halogen atom, m is a number defined by $0<m\leq3$, n is a number defined by $0\leq n<3$, p is a number defined by $0\leq p<3$ and q is a number defined by $0\leq q<3$, provided that $m+n+p+q=3$.)

(C-1b): Alkyl complexes of periodic table Group 1 metals with aluminum represented by the general formula $M^2 Al R^a_4$ (wherein, $M^2$ represents Li, Na or K, and $R^a$ represents a hydrocarbon group having 1 to 15 carbon atoms, preferably 1 to 4 carbon atoms.)

(C-1c): Dialkyl compounds having metallic atoms belonging to the periodic table Group 2 or 12 represented by the general formula $R^a R^b M^3$ (wherein, $R^a$ and $R^b$ may be the same or different each other and each represents a hydrocarbon group having 1 to 15 carbon atoms, preferably 1 to 4 carbon atoms, and $M^3$ is Mg, Zn or Cd.)

As the above-described organoaluminum compound (C-1a), the following compounds can be used for example:

Organoaluminum compounds represented by the general formula $R^a_m Al(OR^b)_{3-m}$ (wherein, $R^a$ and $R^b$ may be the same or different from each other and each represents a hydrocarbon group having 1 to 15 carbon atoms, preferably 1 to 4 carbon atoms, and m is preferably a number defined by $1.5\leq m\leq 3$.);

Organoaluminum compounds represented by the general formula $R^a_m AlX_{3-m}$ (wherein, $R^a$ represents a hydrocarbon group having 1 to 15 carbon atoms, preferably 1 to 4 carbon atoms, X represents a halogen atom, and m is preferably a number defined by $0<m<3$.);

Organoaluminum compounds represented by the general formula $R^a_m AlH_{3-m}$ (wherein, $R^a$ represents a hydrocarbon group having 1 to 15 carbon atoms, preferably 1 to 4 carbon atoms, and m is preferably a number defined by $2\leq m<3$.); and Organoaluminum compounds represented by the general formula $R^a_m Al(OR^b)_n X_q$ (wherein, $R^a$ and $R^b$ may be the same or different from each other and each represents a hydrocarbon group having 1 to 15 carbon atoms, preferably 1 to 4 carbon atoms, X represents a halogen atom, m is a number defined by $0<m\leq3$, n is a number defined by $0\leq n<3$ and q is a number defined by $0\leq q<3$, provided that $m+n+q=3$.).

Concrete examples of the above-described organoaluminum compounds (C-1a) include tri(n-alkyl)aluminums such as trimethylaluminum, triethylaluminum, tri(n-butyl)aluminum, tripropylaluminum, tripentylaluminum, trihexylaluminum, trioctylaluminum and tridecylaluminum; tri-branched alkylaluminums such as triisopropylaluminum, triisobutylaluminum, tri(sec-butyl)aluminum, tri(tert-butyl)aluminum, tri(2-methylbutyl)aluminum, tri(3-methylbutyl)aluminum, tri(2-methylpentyl)aluminum, tri(3-methylpentyl) aluminum, tri(4-methylpentyl)aluminum, tri(2-methylhexyl)aluminum, tri(3-methylhexyl)aluminum and tri(2-ethylhexyl) aluminum; tricycloalkylaluminums such as tricyclohexylaluminum and tricyclooctylaluminum; triarylaluminums such as triphenylaluminum and tritolylaluminum; dialkylaluminum hydrides such as diethylaluminum hydride and diisobutylaluminum hydride; alkenylaluminums represented by $(iC_4H_9)_x Al_y (C_5H_{10})_z$ (wherein, x, y and z are positive numbers, $z\geq 2x$, and $iC_4H_9$ represents an isobutyl group) such as isoprenylaluminum; alkylaluminum alkoxides such as isobutylaluminum methoxide, isobutylaluminum ethoxide and isobutylaluminum isopropoxide; dialkylaluminum alkoxides such as dimethylaluminum methoxide, diethylaluminum ethoxide and dibutylaluminum butoxide; alkylaluminum sesqui alkoxides such as ethylaluminum sesqui ethoxide and butylaluminum sesqui butoxide; partially alkoxylated alkylaluminums having, for example, an average composition represented by $R^a_{2.5} Al(OR^b)_{0.5}$ (wherein, $R^a$ and $R^b$ may be the same or different from each other and each represents a hydrocarbon group having 1 to 15 carbon atoms, preferably 1 to 4 carbon atoms); dialkylaluminum aryloxides such as diethylaluminum phenoxide, diethylaluminum(2,6-di-tert-butyl-4-methyl phenoxide), ethylaluminumbis(2,6-di-tert-butyl-4-methyl phenoxide), diisobutylaluminum(2,6-di-tert-butyl-4-methyl phenoxide) and isobutylaluminumbis(2,6-di-tert-butyl-4-methyl phenoxide); dialkylaluminum halides such as dimethylaluminum chloride, diethylaluminum chloride, dibutylaluminum chloride, diethylaluminum bromide and diisobutylaluminum chloride; alkylaluminum sesqui halides such as ethylaluminum sesqui chloride, butylaluminum sesqui chloride and ethylaluminum sesqui bromide; partially halogenated alkylaluminums like alkylaluminum dihalides such as ethylaluminum dichloride, propylaluminum dichloride and butylaluminum dibromide; dialkylaluminum hydrides such as diethylaluminum hydride and dibutylaluminum hydride; partially hydrogenated alkylaluminums like alkylaluminum dihydrides such as ethylaluminum dihydride and propylaluminum dihydride; and partially alkoxylated and halogenated alkylaluminums such as ethylaluminumethoxy chloride, butylaluminumbutoxy chloride and ethylaluminumethoxy bromide.

Compounds similar to the organoaluminum compound (C-1a), for example, organoaluminum compounds in which 2 or more aluminum compounds are bonded via a nitrogen atom like $(C_2H_5)_2 AlN(C_2H_5)Al(C_2H_5)_2$ can also be used.

Concrete examples of the above-described compound (C-1 b) include $LiAl(C_2H_5)_4$ and $LiAl(C_7H_{15})_4$.

Concrete examples of the above-described compound (C-1c) include dimethylmagnesium, diethylmagnesium, dibutylmagnesium and butylethylmagnesium.

Concrete examples of the organometal compound (C-1) other than the compounds (C-1a) to (C-1c) described above include methyllithium, ethyllithium, propyllithium, butyllithium, methylmagnesium bromide, methylmagnesium chloride, ethylmagnesium bromide, ethylmagnesium chloride, propylmagnesium bromide, propylmagnesium chloride, butylmagnesium bromide and butylmagnesium chloride.

A combination of halogenated aluminum and alkyllithium or a combination of halogenated aluminum and alkylmagnesium can also be used, for example, so as to form organoaluminum compounds in the oligomerization reaction system.

The organometal compounds (C-1) described above can be used singly or in combination of two or more thereof. Regarding the organometal compounds (C-1) as described above, the organoaluminum compound (C-1a) is particularly preferable.

[Organoaluminumoxy Compound (C-2)]

The organoaluminumoxy compounds (C-2) may be conventionally known aluminoxanes, or may be benzene-insoluble organoaluminumoxy compounds as disclosed in Japanese Patent Publication No. H02-078687 (1990), as JP 1990078687(A). The conventionally known aluminoxane can be produced, for example, by the following methods, and usually obtained in the form of a solution.

(1) A method comprising adding an organoaluminum compound such as trialkylaluminum to a suspension comprising a hydrocarbon solvent and a compound having adsorbed water or a crystal water-containing salt (for example, magnesium chloride hydrate, copper sulfate hydrate, aluminum sulfate hydrate, nickel sulfate hydrate, first cerium chloride hydrate, i. e., cerium (III) chloride hydrate) and causing reaction of the adsorbed water or crystal water with the organoaluminum compound.

(2) A method comprising allowing water, ice or moisture vapor to act directly on an organoaluminum compound such as trialkylaluminum in a solvent such as benzene, toluene, ethyl ether and tetrahydrofuran.

(3) A method comprising reacting an organotin oxide such as dimethyltin oxide and dibutyltin oxide with an organoaluminum compound, such as trialkylaluminum in a solvent such as decane, benzene and toluene.

The aluminoxane may contain a small amount of an organometal component. The solvent and the unreacted organoaluminum compound may be removed by distillation from the solution of the aluminoxane collected in each of the above methods. Then, the aluminoxane thus obtained may be further re-dissolved in the solvent, or alternatively suspended in a poor solvent for the aluminoxane.

Concrete examples of the organoaluminum compound usable for production of the aluminoxane are the same as the concrete examples of the organoaluminum compound (C-1a) described previously. The organoaluminum compounds may be used singly or in combination of two or more thereof. Preferable examples thereof include trialkylaluminum and tricycloalkylaluminum, wherein trimethylaluminum is particularly preferable.

As the solvent for production of the aluminoxane, for example, hydrocarbon solvents and ether solvents can be used. Concrete examples of the hydrocarbon solvent include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosene and light oil; and halides of aromatic hydrocarbons, aliphatic hydrocarbons or alicyclic hydrocarbons (particularly, chlorides or bromides). Concrete examples of the ether solvent include ethyl ether and tetrahydrofuran. Among them, aromatic hydrocarbons and aliphatic hydrocarbons are preferable. When an organoaluminumoxy compound insoluble or sparingly soluble in benzene is used, the amount of the Al component dissolved in benzene at 60° C. is usually 10% or less, preferably 5% or less, more preferably 2% in terms of Al atom.

As the organoaluminumoxy compound (C-2), organoaluminumoxy compounds containing boron represented by the following general formula (5) can also be used.

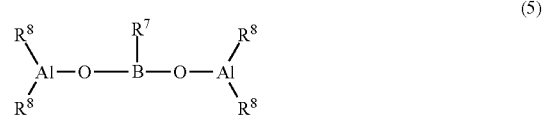

(5)

(in the general formula (5), $R^7$ represents a hydrocarbon group having 1 to 10 carbon atoms. Groups $R^8$ may be the same or different from each other and each represents a hydrogen atom, a halogen atom or a hydrocarbon group having 1 to 10 carbon atoms.)

The organoaluminumoxy compound containing boron represented by the general formula (5) can be produced, for example, by reacting alkylboronic acid represented by the following general formula (6) and an organoaluminum compound under an inert gas atmosphere in an inert solvent at a temperature of −80° C. to room temperature for 1 minute to 24 hours.

(6)

(in the general formula (6), $R^7$ represents the same group as $R^7$ in the above-described general formula (5))

Concrete examples of the alkylboronic acid represented by the general formula (6) include methylboronic acid, ethylboronic acid, isopropylboronic acid, n-propylboronic acid, n-butylboronic acid, isobutylboronic acid, n-hexylboronic acid, cyclohexylboronic acid, phenylboronic acid, 3,5-difluorophenylboronic acid, pentafluorophenylboronic acid and 3,5-bis(trifluoromethyl)phenylboronic acid. Regarding the above examples, methylboronic acid, n-butylboronic acid, isobutylboronic acid, 3,5-difluorophenylboronic acid and pentafluorophenylboronic acid are preferable. These alkylboronic acids can be used singly or in combination of two or more thereof.

Concrete examples of the organoaluminum compound to be reacted with alkylboronic acid are the same as the concrete examples of the organoaluminum compound (C-1a) described previously. The organoaluminum compounds can be used singly or in combination of two or more thereof. Among them, trialkylaluminum and tricycloalkylaluminum are preferable, and trimethylaluminum, triethylaluminum and triisobutylaluminum are more preferable.

The organoaluminumoxy compounds (C-2) described above can be used singly or in combination of two or more thereof.

[Ionized Ionic Compound (C-3)]

The ionized ionic compounds (C-3) are those to form an ion pair by reacting with a transition metal compound. Therefore, the compounds, which have a property to form an ion pair by contacting at least with a transition metal compound, correspond to the ionized ionic compounds (C-3).

As the ionized ionic compound (C-3), for example, Lewis acids, ionic compounds, borane compounds and carborane compounds can be used, as described in Japanese Patent Publication No. H01-501950 (1989) as JP 1989501950 (A), Japanese Patent Publication No. H01-502036 (1989) as JP 1989502036 (A), Japanese Patent Publication No. H03-179005 (1991) as JP 1991179005 (A), Japanese Patent Publication No. H03-179006 (1991) as JP 1991179006 (A), Japanese Patent Publication No. H03-207703 (1991) as JP 1991207703 (A), Japanese Patent Publication No. H03-207704 (1991) as JP 1991207704 (A) and U.S. Pat. No. 5,321,106.

Further, heteropoly acid compounds and isopoly acid compounds can also be used.

The above-described Lewis acid includes, for example, compounds represented by the general formula $BR_3$ (R is a phenyl group or fluorine atom optionally having a substituent(s) such as fluorine, methyl group and trifluoromethyl group). Concrete examples thereof include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethylphenyl)boron.

Concrete examples of the above-described ionic compound include, for example, compounds represented by the following general formula (7).

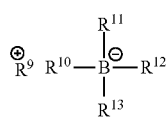

(7)

In the general formula (7), $R^{9+}$ includes, for example, $H^+$, carbonium cation, i. e., carbocaion, oxonium cation, ammonium cation, phosphonium cation, cycloheptyltrienyl cation and ferrocenium cation having a transition metal. $R^{10}$ to $R^{13}$ may be the same or different from each other and each represents an organic group, preferably an aryl group or a substituted aryl group.

When $R^{9+}$ is a carbonium cation, concrete examples thereof include trisubstituted carbonium cations such as a triphenylcarbonium cation, i. e., a triphenylcarbenium ion, a tri(methylphenyl)carbonium cation, i. e., a tri(methylphenyl)carbenium ion and a tri(dimethylphenyl)carbonium cation, i. e., a tri(dimethylphenyl)carbenium ion.

When $R^{9+}$ is an ammonium cation, concrete examples thereof include trialkylammonium cations such as a trimethylammonium cation, a triethylammonium cation, a tri(n-propyl)ammonium cation and a tri(n-butyl)ammonium cation; N,N-dialkylanilinium cations such as an N,N-dimethylanilinium cation, an N,N-diethylanilinium cation and an N,N-2,4,6-pentamethylanilinium cation; and dialkylammonium cations such as a di(isopropyl)ammonium cation and a dicyclohexylammonium cation.

When $R^{9+}$ is a phosphonium cation, concrete examples thereof include triarylphosphonium cations such as a triphenylphosphonium cation, a tri(methylphenyl)phosphonium cation and a tri(dimethylphenyl)phosphonium cation.

$R^{9+}$ is preferably a carbonium cation or an ammonium cation, more preferably a triphenylcarbonium cation, an N,N-dimethylanilinium cation or an N,N-diethylanilinium cation.

As the ionic compounds other than the compounds represented by the general formula (7) described above, a trialkyl-substituted ammonium salt, an N,N-dialkylanilinium salt, a dialkylammonium salt and a triarylphosphonium salt can also be used.

Concrete examples of the above-described trialkyl-substituted ammonium salt include triethylammonium tetraphenylborate, tri(n-propyl)ammonium tetraphenylborate, tri(n-butyl)ammonium tetraphenylborate, trimethylammonium tetra(p-tolyl)borate, trimethylammonium tetra(o-tolyl)borate, tri(n-butyl)ammonium tetra(pentafluorophenyl)borate, tri(n-propyl)ammonium tetra(o,p-dimethylphenyl)borate, tri(n-butyl)ammonium tetra(m,m-dimethylphenyl)borate, tri(n-butyl)ammonium tetra(p-trifluoromethylphenyl)borate, tri(n-butyl)ammonium tetra(3,5-ditrifluoromethylphenyl) borate and tri(n-butyl)ammonium tetra(o-tolyl)borate.

Concrete examples of the above-described N,N-dialkylanilinium salt include N,N-dimethylanilinium tetraphenylborate, N,N-diethylanilinium tetraphenylborate and N,N,2,4,6-pentamethylanilinium tetraphenylborate.

Concrete examples of the above-described dialkylammonium salt include di(n-propyl)ammonium tetra(pentafluorophenyl)borate and dicyclohexylammonium tetraphenylborate.

As the ionic compounds other than the above salts, the usable salts also include triphenylcarbenium tetrakis(pentafluorophenyl)borate, N,N-dimethylanilinium tetrakis(pentafluorophenyl)borate, ferrocenium tetra(pentafluorophenyl) borate, triphenylcarbenium pentaphenylcyclopentadienyl complex, N,N-diethylanilinium pentaphenylcyclopentadienyl complex, and boron compounds represented by the following general formula (8) or (9):

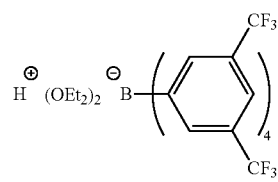

(8)

(in the general formula (8), Et represents an ethyl group.)

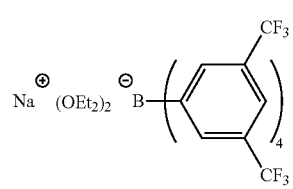

(9)

(in the general formula (9), Et represents an ethyl group.)

Concrete examples of the above-described borane compound include decaborane(14); salts of anions such as bis[tri(n-butyl)ammonium] nonaborate, bis[tri(n-butyl)ammonium] decaborate, bis[tri(n-butyl)ammonium] undecaborate, bis[tri(n-butyl)ammonium] dodecaborate, bis[tri(n-butyl)ammonium]decachlorodecaborate, bis[tri(n-butyl) ammonium] dodecachlorododecaborate; salts of metal borane anions such as tri(n-butyl)ammonium bis(dodecahydridedodecaborate)cobaltate (III) and bis[tri(n-butyl)ammonium]bis(dodecahydridedodecaborate)nickelate (III).

Concrete examples of the above-described carborane compound include salts of anions such as 4-carbanonaborane(14), 1,3-dicarbanonaborane(13), 6,9-dicarbadecaborane(14), dodecahydride-1-phenyl-1,3-dicarbanonaborane, dodecahydride-1-methyl-1,3-dicarbanonaborane, undecahydride-1,3-dimethyl-1,3-dicarbanonaborane, 7,8-dicarbaundecaborane(13), 2,7-dicarbaundecaborane(13), undecahydride-7,8-dimethyl-7,8-dicarbaundecaborane, dodecahydride-11-methyl-2,7-dicarbaundecaborane, tri(n-butyl)ammonium 1-carbadecaborate, tri(n-butyl)ammonium 1-carbaundecaborate, tri(n-butyl)ammonium 1-carbadodecaborate, tri(n-butyl)ammonium 1-trimethylsilyl-1-carbadecaborate, tri(n-butyl)ammoniumbromo 1-carbadodecaborate, tri(n-butyl)ammonium 6-carbadecaborate (14), tri(n-butyl)ammonium 6-carbadecaborate(12), tri(n-butyl) ammonium 7-carbaundecaborate(13), tri(n-butyl)ammonium 7,8-dicarbaundecaborate(12), tri(n-butyl)ammonium 2,9-dicarbaundecaborate(12), tri(n-butyl)ammonium dodecahydride-8-methyl-7,9-dicarbaundecaborate, tri(n-butyl) ammonium undecahydride-8-ethyl-7,9-dicarbaundecaborate, tri(n-butyl)ammonium undecahydride-8-butyl-7,9-dicarbaundecaborate, tri(n-butyl)ammonium undecahydride-8-allyl-7,9-dicarbaundecaborate, tri(n-butyl)ammonium undecahydride-9-trimethylsilyl-7,8-dicarbaundecaborate and tri(n-butyl)ammonium undecahydride-4,6-dibromo-7-carbaundecaborate; and salts of metal carborane anions such as tri(n-butyl)ammonium bis(nonahydride-1,3-dicarbanonaborate)cobaltate (III), tri(n-butyl)ammonium bis(undecahydride-7,8-dicarbaundecaborate)ferrate (III), tri(n-butyl) ammonium bis(undecahydride-7,8-dicarbaundecaborate) cobaltate (III), tri(n-butyl)ammonium bis(undecahydride-7,8-dicarbaundecaborate)nickelate (III), tri(n-butyl)ammonium bis(undecahydride-7,8-dicarbaundecaborate)cuprate (III), tri(n-butyl)ammonium bis(undecahydride-7,8-dicarbaundecaborate)aurate (III), tri(n-butyl)ammonium bis(nonahydride-7,8-dimethyl-7,8-dicarbaundecaborate)ferrate (III), tri(n-butyl)ammonium bis(nonahydride-7,8-dimethyl-7,8-dicarbaundecaborate)chromate (III), tri(n-butyl)ammonium bis(tribromooctahydride-7,8-dicarbaundecaborate)cobaltate (III), tris[tri(n-butyl)ammonium] bis(undecahydride-7-carbaundecaborate)chromate (III), bis[tri(n-butyl)ammonium] bis(undecahydride-7-carbaundecaborate)manganate (IV), bis[tri(n-butyl)ammonium] bis(undecahydride-7-carbaundecaborate)cobaltate (III) and bis[tri(n-butyl)ammonium] bis(undecahydride-7-carbaundecaborate)nickelate (IV).

The above-described heteropoly acid compound is generally comprising a silicon, phosphorus, titanium, germanium, arsenicum or tin atom; and one or more atoms selected from vanadium, niobium, molybdenum and tungsten. Concrete examples thereof include phosphovanadic acid, germanovanadic acid, arsenovanadic acid, phosphoniobic acid, germanoniobic acid, siliconomolybdic acid, phosphomolybdic acid, titanomolybdic acid, germanomolybdic acid, arsenomolybdic acid, stannomolybdic acid, phosphotungstic acid, germanotungstic acid, stannotungstic acid, phosphomolybdovanadic acid, phosphotungstovanadic acid, germanotungstovanadic acid, phosphomolybdotungstovanadic acid, germanomolybdotungstovanadic acid, phosphomolybdotungstic acid and phosphomolybdoniobic acid. In addition, salts of these acids may also be permissible. Concrete examples of the salts include, for example, salts with periodic table Group 1 or 2 metals (for example, lithium, sodium, potassium, rubidium, cesium, beryllium, magnesium, calcium, strontium and barium), organic salts such as triphenylethyl salts, and isopoly compounds.

The ionized ionic compounds (C-3) described above can be used singly or in combination of two or more thereof.

When the olefin oligomerization catalyst described above is used, an olefin oligomer is obtained with a high catalytic activity. When ethylene is particularly used as the olefin, the selectivity of 1-octene is high. For example, when an organoaluminumoxy compound (C-2) such as methylaluminoxane is used together as a cocatalyst component, a higher catalytic activity on ethylene is obtained and, thus, 1-octene can be produced. Further, also when an ionized ionic compound (C-3) such as triphenylcarbonium tetrakis(pentafluorophenyl)borate is used as a cocatalyst component, 1-octene is obtained from ethylene with a better catalytic activity and a higher selection rate.

<Carrier (D)>

The olefin oligomerization catalyst of the present invention may contain a carrier (D). The carrier (D) comprises an inorganic compound or an organic compound, and generally formed as solid granulates or solid fine particulates. In the present invention, the carrier (D) supports or carries a chromium compound (A), an amine compound (B) and/or a compound (C). The preferable inorganic compounds include porous oxides, inorganic halides, clays, clay minerals and ion-exchangeable layered compounds.

Concrete examples of the above-described porous oxide include $SiO_2$, $Al_2O_3$, $MgO$, $ZrO$, $TiO_2$, $B_2O_3$, $CaO$, $ZnO$, $BaO$ and $ThO_2$, or a composite or a mixture containing them (for example, natural or synthetic zeolite, $SiO_2$—$MgO$, $SiO_2$—$Al_2O_3$, $SiO_2$—$TiO_2$, $SiO_2$—$V_2O_5$, $SiO_2$—$Cr_2O_3$, $SiO_2$—$TiO_2$—$MgO$). Among them, porous oxides containing $SiO_2$ and/or $Al_2O_3$ as the main component are preferable. The porous oxide may contain a small amount of carbonic acid salts, sulfuric acid salts, nitric acid salts or oxide components such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$. The particle size, the specific surface area and the pore volume of the porous oxide are not particularly restricted, and may be appropriately determined depending on the kind of the material and the production method. In the present invention, the particle size of the porous oxide is preferably 0.5 to 300 μm, more preferably 20 to 200 μm. The specific surface area thereof is preferably 50 to 1000 $m^2/g$, more preferably 100 to 700 $m^2/g$, and the pore volume thereof is preferably 0.3 to 3.0 $cm^3/g$. If necessary, the porous oxide is calcined at preferably 100 to 1000° C., more preferably 150 to 700° C.

Concrete examples of the above-described inorganic halide include $MgCl_2$, $MgBr_2$, $MnCl_2$ and $MnBr_2$. The inorganic halide may be used as it is or may be crushed with a ball mill or a vibration mill before use. In addition, the inorganic halide can be dissolved in a solvent such as alcohols, then, deposited in the form of fine particles with a depositing agent, and the resultant deposit can be used.

The above-described clay usually contains clay minerals as the main component. The above-described ion-exchangeable layered compounds are those having a crystal structure, in which planes formed by ionic bonds are laminated in parallel with each other, with a weak binding force, while contained ions are exchangeable. As the ion-exchangeable layered compound, for example, ion crystalline compounds having a layered crystal structure such as hexagonal close-packed type, antimony type, $CdCl_2$ type and $CdI_2$ type can be used. The majority of the clay minerals are the ion-exchangeable layered compounds. These clays, clay minerals and ion-exchangeable layered compounds are not limited to natural ones, and artificial synthetic products can also be used.

Concrete examples of the clays and clay minerals include kaolin, bentonite, "Kibushi" clay, "Gairome" clay, allophane, hisingerite, pyrophyllite, mica, montmorillonite, vermiculite, hectorite, taeniolite, chlorite, palygorskite, kaolinite, nacrite, dickite and halloysite. Concrete examples of the ion-exchangeable layered compound include crystalline acidic salts of polyvalent metals such as α-Zr(HAsO$_4$)$_2$.H$_2$O, α-Zr(KPO$_4$)$_2$.3H$_2$O, α-Ti(HPO$_4$)$_2$, α-Ti(HAsO$_4$)$_2$.H$_2$O, α-Sn(HPO$_4$)$_2$.H$_2$O, γ-Zr(HPO$_4$)$_2$, γ-Ti(HPO$_4$)$_2$ and γ-Ti(NH$_4$PO$_4$)$_2$.H$_2$O. Among them, clays and clay minerals are preferable, and synthetic mica, montmorillonite, vermiculite, hectorite and taeniolite are more preferable.

The pore volume of the clay, clay mineral and ion-exchangeable layered compound is preferably 0.1 cc/g or more, more preferably 0.3 to 5 cc/g. This pore volume is measured in the pore radius range of 20 Å to 3×10$^4$ Å by a mercury intrusion technique using a mercury porosimeter. When a material with a pore volume less than 0.1 cc/g in pore radiuses of 20 Å or more is used as the carrier, there is a tendency that it is difficult to obtain high oligomerization activities.

It is also preferable to subject the clay and the clay mineral to a chemical treatment. The chemical treatment includes, for example, a surface treatment that removes impurities adhering to the surface and a treatment that affects the crystal structure of the clay. Concrete examples of the chemical treatment include an acid treatment, an alkali treatment, a salt treatment and an organic substance treatment. The acid treatment not only removes impurities on the surface but also can increase the surface area by eluting cations such as Al, Fe and Mg in the crystal structure. The alkali treatment can destroy the crystal structure of the clay and change the structure of the clay. According to the salt treatment and the organic substance treatment, the surface area and the interlayer distance can be changed by forming an ionic complex, a molecular complex or an organic derivative.

The ion-exchangeable layered compound may be a layered compound in a state where a space(s) between the layers is expanded by exchanging the exchangeable ions between the layers with another large bulky ion. This bulky ion plays a role as a rod supporting the layered structure and is usually called a pillar. Moreover, introducing another substance between the layers of the layered compound in this way is called intercalation. Concrete examples of the guest compound (another substance) to be intercalated include cationic inorganic compounds such as TiCl$_4$ and ZrCl$_4$, metal alkoxides such as Ti(OR)$_4$, Zr(OR)$_4$, PO(OR)$_3$ and B(OR)$_3$ (R is a hydrocarbon group, etc.), and metal hydroxide ions such as [Al$_{13}$O$_4$(OH)$_{24}$]$^{7+}$, [Zr$_4$(OH)$_{14}$]$^{2+}$ and [Fe$_3$O(OCOCH$_3$)$_6$]$^+$. The guest compounds can be used singly or in combination of two or more thereof. When the guest compound is intercalated, for example, dimers obtained by hydrolysis of metal alkoxides such as Si(OR)$_4$, Al(OR)$_3$ and Ge(OR)$_4$ (R is a hydrocarbon group, etc.) and colloidal inorganic compounds such as SiO$_2$ can coexist. Concrete examples of the pillar include an oxide generated by heat dehydration after intercalation of the above-described metal hydroxide ions between layers.

The clay, the clay mineral and the ion-exchangeable layered compound may be used as they are, or may be used after processing such as ball milling and sieving. Further, they may be used after newly adding and adsorbing water, or may be used after heat dehydration treatments.

The above-described organic compound includes, for example, granulated or particulate solid organic compounds having particle sizes of 10 to 300 μm. Concrete examples of monomers of the polymer forming the organic compound include (co)dimers generated mainly from an α-olefin having 2 to 14 carbon atoms such as ethylene, propylene, 1-butene and 4-methyl-1-pentene, (co)dimers generated mainly from vinylcyclohexane or styrene, and modified products thereof.

<Organic Compound Component (E)>

The olefin oligomerization catalyst of the present invention may further contain an organic compound component (E), if necessary.

In the present invention, the organic compound component (E) is used, for example, for the purpose of improving an oligomerization performance. As the organic compound, for example, alcohols, phenolic compounds, carboxylic acids, phosphorus compounds and sulfonic acid salts can be used. But, the organic compound component (E) is not limited to them.

As the above-described alcohols and the above-described phenolic compound, compounds represented by R$^{14}$—OH are usually used. R$^{14}$ represents a hydrocarbon group having 1 to 50 carbon atoms or a halogenated hydrocarbon group having 1 to 50 carbon atoms. As the alcohols, compounds in which R$^{14}$ is a halogenated hydrocarbon are preferable. As the phenolic compound, compounds in which α,α'-position of a hydroxyl group is substituted with a hydrocarbon group having 1 to 20 atoms are preferable.

As the above-described carboxylic acid, compounds represented by R$^{15}$—COOH are generally used. R$^{15}$ represents a hydrocarbon group having 1 to 50 carbon atoms or a halogenated hydrocarbon group having 1 to 50 carbon atoms. Compounds, in which R$^{15}$ is a halogenated hydrocarbon group having 1 to 50 carbon atoms are particularly preferable.

As the above-described phosphorus compound, phosphoric acids having a P—O—H bond and phosphate compounds or phosphine oxide compounds having a P—OR bond or P=O bond are preferable.

As the above-described sulfonic acid salt, for example, compounds represented by the following general formula (10) can be used.

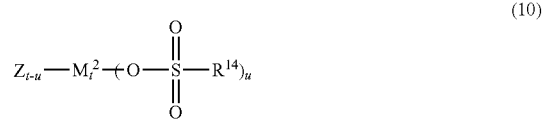

(10)

In the general formula (10), M$^2$ is a periodic table Group 1 to 14 element, R$^{14}$ is hydrogen, a hydrocarbon group having 1 to 20 carbon atoms or a halogenated hydrocarbon group having 1 to 20 carbon atoms, Z is a hydrogen atom, a halogen atom, a hydrocarbon group having 1 to 20 carbon atoms or a halogenated hydrocarbon group having 1 to 20 carbon atoms, t is an integer of 1 to 7, u is an integer defined by 1≤u≤7, and t−u≥1.

<Olefin Oligomerization Catalyst>

The olefin oligomerization catalyst of the present invention is used for the olefin oligomerization reaction. Concrete examples of the olefin include vinyl compounds such as ethylene, propylene, 1-butene, 1-pentene, 1-hexene, 4-methyl-1-pentene, vinylcyclohexene, styrene, 1-octene and 1-decene, and internal olefins such as 2-butene, cyclopentene, cyclohexene and norbornene. Regarding these compounds, ethylene is preferred. Two or more different olefins may be co-oligomerized.

<Production Method of Olefin Oligomer>

The method for producing an olefin oligomer according to the present invention comprises performing an oligomerization reaction of an olefin (preferably trimerization to tetramerization reaction, more preferably tetramerization reaction) in the presence of the olefin oligomerization catalyst described above.

Concrete examples of the olefin to be oligomerized are as described above, and ethylene is especially preferable. Specifically, it is preferable to produce an oligomer by an oligomerization reaction of ethylene. It is more preferable to produce 1-hexene and 1-octene with a high selection rate by trimerization and tetramerization reactions of ethylene. It is particularly preferable to produce 1-octene with a high selection rate by a tetramerization reaction of ethylene.

The order of adding the components for oligomerization into a reaction vessel is not particularly restricted, which components comprises a chromium compound (A), an amine compound (B), a compound (C) and other components [for example, carrier (D), organic compound component (E)] described above. Concrete examples of the method of adding the components are as described below.

(1) A method comprising supplying a component (A) and a component (B), as they are, into a rector, at any order.

(2) A method comprising supplying a transition metal complex into a reaction vessel, which is previously formed by bringing a component (A) into contact with a component (B).

(3) A method comprising supplying a component (A), a component (B) and a component (C), as they are, into a reaction vessel, at any order.

(4) A method comprising forming previously a transition metal complex by bringing a component (A) into contact with a component (B), and supplying the transition metal complex and component (C) into a reaction vessel, at any order.

(5) A method comprising forming previously a transition metal complex by bringing a component (A) into contact with a component (B), preparing a catalyst component by bringing the transition metal complex into contact with a component (C), and supplying the catalyst component into a reaction vessel.

(6) A method comprising forming previously a transition metal complex by bringing a component (A) into contact with a component (B), preparing a catalyst component by bringing the transition metal complex into contact with a component (C), and supplying the catalyst component and a component (C), into a reaction vessel, at any order. In this case, these components (C) may be the same or different from each other.

(7) A method comprising supplying a carrier (D) carrying a transition metal complex previously formed by bringing a component (A) into contact with a component (B), into a reaction vessel.

(8) A method comprising supplying a component (C) and a carrier (D) carrying a transition metal complex previously formed by bringing a component (A) into contact with a component (B), into a reaction vessel, at any order.

(9) A method comprising supplying a carrier (D) carrying a component (C) and a transition metal complex previously formed by bringing a component (A) into contact with a component (B), into a reaction vessel.

(10) A method comprising supplying a component (C) and a carrier (D) carrying a component (C) and a transition metal complex previously formed by bringing a component (A) into contact with a component (B), into a reaction vessel, at any order. In this case, these components (C) may be the same or different from each other.

(11) A method comprising supplying a component (A), a component (B) and a carrier (D) carrying a component (C) into a reaction vessel at any order.

(12) A method comprising supplying a carrier (D) carrying a component (C) and a transition metal complex previously formed by bringing a component (A) into contact with a component (B), into a reaction vessel, at any order.

(13) A method comprising supplying a component (A), a component (B), a component (C) and a carrier (D) carrying a component (C), into a rector, at any order. In this case, these components (C) may be the same or different from each other.

(14) A method comprising supplying a component (C), a carrier (D) carrying a component (C) and a transition metal complex previously formed by bringing a component (A) into contact with a component (B), into a reaction vessel, at any order. In this case, these components (C) may be the same or different from each other.

(15) A method comprising supplying a carrier (D) carrying a transition metal complex previously formed by bringing a component (A) into contact with a component (B) and the other carrier (D) carrying a component (C), into a reaction vessel, at any order.

(16) A method comprising supplying a component (C), a carrier (D) carrying a transition metal complex previously formed by bringing a component (A) into contact with a component (B) and the other carrier (D) carrying a component (C), into a reaction vessel, at any order. In this case, these components (C) may be the same or different.

(17) A method comprising supplying a component (A), a component (B) and a component (E), as they are, into a reaction vessel, at any order.

(18) A method comprising supplying a component (E) and a transition metal complex previously formed by binging a component (A) into contact with a component (B), into a reaction vessel, at any order.

(19) A method comprising supplying a component (A), a component (B), a component (C) and a component (E), as they are, into a reaction vessel, at any order.

(20) A method comprising supplying a component (C), a component (E) and a transition metal complex previously formed by bringing a component (A) into contact with a component (B), into a reaction vessel, at any order.

(21) A method comprising supplying a component (A), a component (B) and a component previously obtained by bringing a component (C) into contact with a component (E), into a reaction vessel, at any order.

(22) A method comprising forming previously a transition metal complex by bringing a component (A) into contact with a component (B) and supplying the transition metal complex and a component previously obtained by bringing a component (C) into contact with a component (E), into a reaction vessel, at any order.

(23) A method comprising supplying a component (A), a component (B) and a carrier (D) carrying a component (E), into a reaction vessel, at any order.

(24) A method comprising forming previously a transition metal complex by bringing a component (A) into contact with a component (B) and supplying the transition metal complex and a carrier (D) carrying a component (E), into a reaction vessel, at any order.

(25) A method comprising supplying a component (A), a component (B) and a carrier (D) carrying a component (C) and a component (E), into a reaction vessel, at any order.

(26) A method comprising forming previously a transition metal complex by bringing a component (A) into contact with a component (B) and supplying the transition metal complex and a carrier (D) carrying a component (C) and a component (E), into a reaction vessel, at any order.

(27) A method comprising forming previously a transition metal complex by bringing a component (A) into contact with a component (B), preparing a catalyst component by bringing the transition metal complex into contact with a component (C), and supplying the catalyst component and a component (E), into a reaction vessel, at any order.

(28) A method comprising forming previously a transition metal complex by bringing a component (A) into contact with a component (B), preparing a catalyst component by bringing the transition metal complex into contact with a component (C), and supplying the catalyst component, a component (C) and a component (E), into a reaction vessel, at any order. In this case, these components (C) may be the same or different from each other.

(29) A method comprising forming previously a transition metal complex by bringing a component (A) into contact with a component (B), preparing a catalyst component by bringing the transition metal complex into contact with a component (C) and supplying the catalyst component and a component previously obtained by bringing a component (C) into contact with a component (E), into a reaction vessel, at any order. In this case, these components (C) may be the same or different from each other.

(30) A method comprising supplying a component (C), a component (E) and a carrier (D) carrying a transition metal complex previously formed by bringing a component (A) into contact with a component (B), into a reaction vessel, at any order.

(31) A method comprising supplying a component (E) and a carrier (D) carrying a transition metal complex previously formed by bringing a component (A) into contact with a component (B), into a reaction vessel, at any order.

(32) A method comprising supplying a carrier (D) and a component previously obtained by bringing a component (C) into contact with a component (E), into a reaction vessel, at any order, wherein the carrier (D) carries a transition metal complex previously formed by bringing a component (A) into contact with a component (B).

(33) A method comprising forming previously a transition metal complex by bringing a component (A) into contact with a component (B), obtaining a catalyst component by bringing a component (E) into contact with the transition metal complex and supplying the catalyst component, into a reaction vessel.

(34) A method comprising forming previously a transition metal complex by bringing a component (A) into contact with a component (B), obtaining a catalyst component by bringing a component (C) and a component (E) into contact with the transition metal complex, at any order, and supplying the catalyst component, into a reaction vessel.

(35) A method comprising forming previously a transition metal complex by bringing a component (A) into contact with a component (B), obtaining a catalyst component by bringing a component (C) and a component (E) into contact with the transition metal complex, at any order, and supplying the catalyst component and a component (C), into a reaction vessel, at any order. In this case, these components (C) may be the same or different from each other.

(36) A method comprising supplying a carrier (D) into a reaction vessel, wherein the carrier (D) carries a component (E) and a transition metal complex previously formed by bringing a component (A) into contact with a component (B).

(37) A method comprising supplying a carrier (D) into a reaction vessel, wherein the carrier (D) carries a component (C), a component (E) and a transition metal complex previously formed by bringing a component (A) into contact with a component (B).

(38) A method comprising supplying a component (C) and a carrier (D) into a reaction vessel, at any order, wherein the carrier (D) carries a component (C), a component (E) and a transition metal complex previously formed by bringing a component (A) into contact with a component (B). In this case, these components (C) may be the same or different from each other.

In the present invention, an olefin oligomer is obtained by oligomerizing an olefin in the presence of the olefin oligomerization catalyst described above. The oligomerization can be carried out by any of liquid phase reaction methods such as solution reaction and suspension reaction, and gas phase polymerization methods.

In the liquid phase reaction method, an inactive hydrocarbon solvent is generally used. Concrete examples of the inactive hydrocarbon solvent include aliphatic hydrocarbons such as propane, butane, isobutane, pentane, isopentane, hexane, heptane, octane, decane, dodecane and kerosene; alicyclic hydrocarbons such as cyclopentane, cyclohexane, methylcyclohexane and methylcyclopentane; aromatic hydrocarbons such as benzene, toluene, xylene, trimethylbenzene and tetralin; halogenated hydrocarbons such as ethylene chloride, chlorobenzene and dichloromethane, or mixtures thereof. Regarding the above compounds, preferable solvents include linear saturated hydrocarbons having 5 to 7 carbon atoms such as pentane, n-hexane and n-heptane; and alicyclic saturated hydrocarbons such as methylcyclohexane.

When 1-hexene and 1-octene are produced, for example, mainly through trimerization to tetramerization reactions of ethylene by using an olefin oligomerization catalyst, the amount of a chromium atom in the component (A) is generally $10^{-12}$ to $10^{-2}$ mol, preferably $10^{-10}$ to $10^{-3}$ mol per liter of the reaction volume. In the present invention, even if the component (A) is used at relatively low concentration, an olefin oligomer can be obtained with a high activity.

The component (B) is used in an amount such that the molar ratio [(B)/M] to a chromium atom (M) in the component (A) is generally 0.1 to 10, preferably 0.5 to 2.

Regarding the component (C), the component (C-1) is used in an amount such that the molar ratio [(C-1)/M] of the component (C-1) to a chromium atom (M) in the component (A) is usually 0.01 to 100000, preferably 0.05 to 50000.

The component (C-2) is used in an amount such that the molar ratio [(C-2)/M] of an aluminum atom in the component (C-2) to a chromium atom (M) in the component (A) is usually 10 to 500000, preferably 20 to 100000.

The component (C-3) is used in an amount such that the molar ratio [(C-3)/M] of the component (C-3) to a chromium atom (M) in the component (A) is generally 1 to 10, preferably 1 to 5.

The component (D) is used in an amount such that the ratio (g/mol) of the mass (g) of the carrier (D) to the mol of a chromium atom (M) in the component (A) is generally 100 to 10000, preferably 1000 to 5000.

When the component (C-1) is used as the component (C), the component (E) is used in an amount such that the molar ratio [(E)/(C-1)] is usually 0.01 to 10, preferably 0.1 to 5. When the component (C-2) is used as the component (C), the component (E) is used in an amount such that the molar ratio [(E)/(C-2)] of the component (E) to an aluminum atom in the component (C-2) is generally 0.001 to 2, preferably 0.005 to 1. When the component (C-3) is used as the component (C), the component (E) is used in an amount such that the molar ratio [(E)/(C-3)] is generally 0.01 to 10, preferably 0.1 to 5.

The oligomerization reaction temperature is usually −50 to 200° C., preferably 0 to 170° C., more preferably 40° C. to 130° C., particularly preferably 50° C. to 120° C. The most preferably lower limit value is 60° C. and the most preferable upper limit value is 100° C. There is a tendency that a higher reaction temperature is advantageous for the catalyst according to the present invention, in that by-production of high-molecular-weight polymers such as polyethylene is suppressed, and in that the intended olefin oligomer (particularly, when ethylene is reacted, 1-hexene and 1-octene) is efficiently produced. In addition, the production efficiency of 1-octene tends to increase. For example, it is known that a reaction for selectively producing 1-hexene or 1-octene from ethylene proceeds according to a metallacycle mechanism. The following reasons why the higher reaction temperature is more effective is presumed:

A high temperature is advantageous in order to form a metallacycle mechanism, and additionally, the overall reaction activity is increased, so that the by-production of polyethylene is suppressed. In addition to the above reason, the catalyst of the present invention has a structure that easily generates 1-hexene and 1-octene.

The reaction pressure is generally in the range from a normal pressure to 10 MPa, preferably from a normal pressure to 6 MPa, more preferably a normal pressure to 5 MPa. The lower limit value thereof is preferably 0.5 MPa, more preferably 0.9 MPa, particularly preferably 1.5 MPa. The most preferable upper limit value thereof is 4 MPa. According to the catalyst of the present invention, there is tendency that the higher the reaction pressure, the higher the production efficiency of 1-octene becomes. It is presumed that 1-octene is obtained via metallacyclononane generated by coordination of two molecules of ethylene to metallacyclopentane and subsequent concerted (or sequential) insertion of ethylene. The reason why the higher reaction pressure is more effective is indefinite, but it is presumed that the structure of the catalyst of the present invention becomes more advantageous for coordination of two ethylene molecules to metallacyclopentene, when the reaction pressure becomes higher.

The oligomerization reaction can be carried out in any of batch, semi-continuous and continuous methods.

The oligomerization reaction may be performed by adding an antistatic agent. Concrete examples of the antistatic agent include polypropylene glycol, polypropylene glycol distearate, ethylenediamine-PEG-PPG-block copolymer, stearyldiethanolamine, lauryldiethanolamine, alkyldiethanolamide, polyoxyalkylene (for example, polyethylene glycol-polypropylene glycol-polyethylene glycol block copolymer (PEG-PPG-PEG)). Among them, polyoxyalkylenes (for example, PEG-PPG-PEG) are preferable. The antistatic agent is used in an amount such that the ratio (g/mol) of the mass (g) to the mole of a chromium atom (M) in the component (A) is usually 100 to 10000, preferably 100 to 1000.

The oligomerization reaction may be performed by adding hydrogen. The pressure of hydrogen for the reaction is generally 0.01 MPa to 5 MPa, preferably 0.01 MPa to 1 MPa.

EXAMPLES

The present invention will be illustrated specifically below based on the synthesis examples and the working examples, but the present invention is not limited to them.

The structures of the compounds obtained in the synthesis examples were determined by the apparatuses including 270 MHz $^1$H NMR (manufactured by JEOL Ltd., Device name: GSH-270) and ICP optical emission spectrometer (manufactured by Agilent Technologies, Device name: Type 720-ES).

The yield of the reaction product and the selection rate of 1-hexene and 1-octene were analyzed by gas chromatography (Shimadzu GC-14A, SHIMADZU CORPORATION, J&W Scientific DB-5 column).

[Catalytic Activity]

The catalytic activity was determined by dividing the mass of the reaction product obtained per unit time by the amount of transition metal atoms (mmol) in the transition metal catalyst component used for the oligomerization.

[Selection Rate of 1-Hexene or 1-Octene]

The selection rate of 1-hexene or 1-octene was determined according to the following equation:

$$S(\%) = Wp/Wr \times 100$$

S (%): selection rate of 1-hexene or 1-octene (mass fraction)

Wr (mass): total mass of products having 4 or more carbon atoms generated by reaction Wp (mass): mass of 1-hexene or 1-octene generated by reaction The synthesis examples of the amine compound (B) and the working examples of ethylene oligomerization are shown below.

(1) Synthesis Example of Amine Compound

Synthesis Example 1

In an enoughly dried 20 mL reaction vessel, 2.1 mL (25.4 mmol) of pyrrolidine and 1.0 mL (13.3 mmol) of a 37% formaldehyde aqueous solution were prepared and stirred at room temperature. After 17 hours, diethyl ether was added to the reaction liquid and the soluble component was extracted. The resultant fraction was dried over anhydrous magnesium sulfate. After magnesium sulfate was removed by filtration, the filtrate was distilled under reduced pressure to remove a solvent. The resultant crude product was distilled under reduced pressure, to obtain 1.32 g (yield: 64%) of an amine compound represented by the following formula (B-2) (hereinafter, referred to as compound (1)).

$^1$H-NMR (270 MHz, CD$_3$COCD$_3$): 3.10 (2H, s), 2.52-2.43 (8H, m), 1.74-1.62 (8H, m) ppm

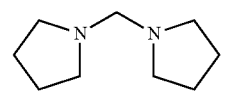

(B-2)

Synthesis Example 2

In an enoughly dried 20 mL reaction vessel, 3.2 mL (27.0 mmol) of 3-methylpiperidine and 1.0 mL (13.3 mmol) of a 37% formaldehyde aqueous solution were prepared at 0° C. and stirred at room temperature. After 18 hours, diethyl ether was added to the reaction liquid and the soluble component was extracted. The resultant fraction was dried over anhydrous magnesium sulfate. After magnesium sulfate was removed by filtration, the filtrate was distilled under reduced pressure to remove a solvent. The resultant crude product was distilled under reduced pressure, to obtain 1.95 g (yield: 70%) of an amine compound represented by the following formula (B-3) (hereinafter, referred to as compound (2)).

$^1$H-NMR (270 MHz, CD$_3$COCD$_3$): 2.92-2.82 (4H, m), 2.74 (2H, s), 1.84-1.73 (2H, m), 1.71-1.37 (10H, m), 0.93-0.86 (2H, m), 0.85 (3H, d, J=1.6 Hz), 0.83 (3H, d, J=1.6 Hz) ppm

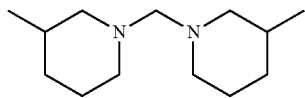

(B-3)

Synthesis Example 3

In an enoughly dried 20 mL reaction vessel, 3.2 mL (26.6 mmol) of 4-methylpiperidine and 1.0 mL (13.3 mmol) of a 37% formaldehyde aqueous solution were prepared at 0° C. and stirred at room temperature. After 17 hours, diethyl ether was added to the reaction liquid and the soluble component was extracted. The resultant fraction was dried over anhydrous magnesium sulfate. After magnesium sulfate was removed by filtration, the filtrate was distilled under reduced pressure to remove a solvent. The resultant crude product was distilled under reduced pressure, to obtain 2.00 g (yield: 71%) of an amine compound represented by the following formula (B-4) (hereinafter, referred to as compound (3)).

$^1$H-NMR (270 MHz, CD$_3$COCD$_3$): 2.98-2.90 (4H, m), 2.76 (2H, s), 1.87-1.76 (4H, m), 1.59-1.54 (4H, m), 1.39-1.23 (2H, m), 1.19-1.04 (4H, m), 0.90 (3H, d, J=2.7 Hz), 0.88 (3H, d, J=2.7 Hz) ppm

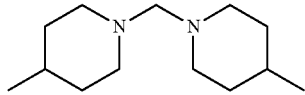

(B-4)

Synthesis Example 4

In an enoughly dried 20 mL reaction vessel, 3.6 mL (42.0 mmol) of N-ethylmethylamine, 0.63 g (20.9 mmol) of p-formaldehyde and 3.4 mL of diethyl ether were prepared and stirred at room temperature. After 92 hours, the reaction liquid was distilled under reduced pressure to remove a solvent, and the resultant crude product was distilled under reduced pressure, to obtain 1.64 g (yield: 60%) of an amine compound represented by the following formula (B-5) (hereinafter, referred to as compound (4)).

$^1$H-NMR (270 MHz, CD$_3$COCD$_3$): 2.79 (2H, s), 2.39 (4H, q, J=7.3 Hz), 2.15 (6H, s), 0.98 (6H, t, J=7.3 Hz) ppm

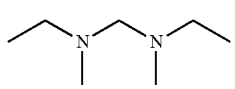

(B-5)

Synthesis Example 5

In an enoughly dried 20 mL reaction vessel, 2.7 mL (26.9 mmol) of N-methylpropylamine, 0.40 g (13.5 mmol) of p-formaldehyde and 1.8 mL of diethyl ether were prepared and stirred at room temperature. After 116 hours, the reaction liquid was distilled under reduced pressure to remove a solvent, and the resultant crude product was distilled under reduced pressure, to obtain 0.95 g (yield: 45%) of an amine compound represented by the following formula (B-6) (hereinafter, referred to as compound (5)).

$^1$H-NMR (270 MHz, CD$_3$COCD$_3$): 2.79 (2H, s), 2.31 (4H, t, J=7.3 Hz), 2.16 (6H, s), 1.44 (4H, sext, J=7.3 Hz), 0.86 (6H, t, J=7.3 Hz) ppm

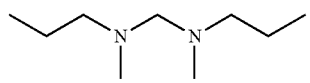

(B-6)

Synthesis Example 6

In an enoughly dried 20 mL reaction vessel, 3.2 mL (27.3 mmol) of N-methylbutylamine, 0.40 g (13.4 mmol) of p-formaldehyde and 1.8 mL of diethyl ether were prepared and stirred at room temperature. After 118 hours, the reaction liquid was distilled under reduced pressure to remove a solvent, and the resultant crude product was distilled under reduced pressure, to obtain 1.96 g (yield: 78%) of an amine compound represented by the following formula (B-7) (hereinafter, referred to as compound (6)).

$^1$H-NMR (270 MHz, CD$_3$COCD$_3$): 2.78 (2H, s), 2.34 (4H, t, J=7.3 Hz), 2.16 (6H, s), 1.48-1.24 (8H, m), 0.89 (6H, t, J=7.3 Hz) ppm

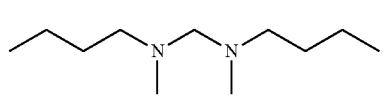

(B-7)

Synthesis Example 7

In an enoughly dried 20 mL reaction vessel, 3.2 mL (26.6 mmol) of N-methylisobutylamine, 0.40 g (13.5 mmol) of p-formaldehyde and 1.8 mL of diethyl ether were prepared and stirred at room temperature. After 94 hours, the reaction liquid was distilled under reduced pressure to remove a solvent, and the resultant crude product was distilled under reduced pressure, to obtain 1.64 g (yield: 65%) of an amine compound represented by the following formula (B-8) (hereinafter, referred to as compound (7)).

$^1$H-NMR (270 MHz, CD$_3$COCD$_3$): 2.77 (2H, s), 2.16 (6H, s), 2.10 (4H, d, J=7.3 Hz), 1.77 (2H, sept, J=6.5 Hz), 0.86 (12H, d, J=6.5 Hz) ppm

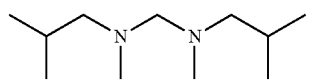

(B-8)

Synthesis Example 8

In an enoughly dried 20 mL reaction vessel, 4.8 mL (26.5 mmol) of N-methyl-n-octylamine, 0.41 g (13.5 mmol) of p-formaldehyde and 1.8 mL of diethyl ether were prepared and stirred at room temperature. After 116 hours, the reaction liquid was distilled under reduced pressure to remove a solvent, and the resultant crude product was distilled under reduced pressure, to obtain 3.19 g (yield: 79%) of an amine compound represented by the following formula (B-9) (hereinafter, referred to as compound (8)).

$^1$H-NMR (270 MHz, CD$_3$COCD$_3$): 2.78 (2H, s), 2.35 (4H, t, J=6.8 Hz), 2.16 (6H, s), 1.44 (4H, t, J=6.8 Hz), 1.29 (20H, brs), 0.87 (6H, t, J=6.8 Hz) ppm

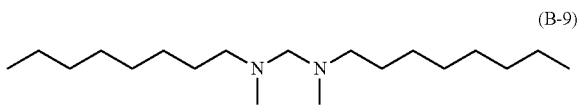 [SMILES: CCCCCCCCN(C)CN(C)CCCCCCCC]
(B-9)

As the other amine compounds, amine compounds (B-1), (B-10) and (B-11) represented by the following formulae (B-1), (B-10) and (B-11) were prepared.

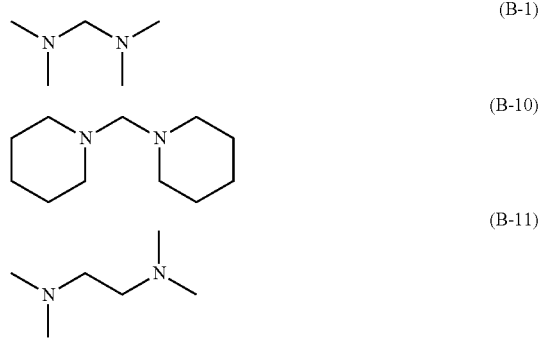
(B-1)
(B-10)
(B-11)

(2) Ethylene Oligomerization

Example 1

In an enoughly dried 100 mL Schlenk flask, 0.45 g (4.38 mmol) of N,N,N',N'-tetramethyldiaminomethane (amine compound (B-1)), 1.62 g (4.18 mmol) of tris(tetrahydrofuran) chromium trichloride and 80 mL of dichloromethane were prepared and stirred for 16 hours under an argon atmosphere. After the reaction liquid was condensed to about ⅓ under reduced pressure, the insoluble component was collected by filtration through a glass filter, and dried under reduced pressure, to obtain 0.79 g of a chromium compound. As a result of analysis, the chromium concentration was 20.0% by mass. Methylcyclohexane was added to this chromium compound, to prepare a methylcyclohexane solution (catalyst solution) at the concentration of 0.001 mmol/mL as a converted value based on the number of chromium atoms.

In a sufficiently nitrogen-purged autoclave having an internal volume of 100 mL, methylaluminoxane (Tosoh Finechem Corporation MMAO-3A, 5.7% by mass hexane solution) was added to 29.6 mL of methylcyclohexane, in an amount of 0.5 mmol as a converted value based on the number of aluminum atoms. Subsequently, 0.10 mL (0.0001 mmol) of the catalyst solution previously prepared was added thereto and the reaction was started under the pressure by ethylene (0.8 MPa-G). Under the same pressure, the reaction proceeded at 60° C. for 60 minutes, while ethylene was supplied. A small amount of isopropanol was added thereto to stop the reaction. After completion of the reaction, the reaction liquid was washed with 0.1 N aqueous solution of hydrochloric acid and pure water, and then, lower boiling point components (components having 10 or less carbon atoms) were separated from higher boiling point components and polyethylene by a liquid nitrogen trap under reduced pressure. The resultant products were analyzed by gas chromatography. The amount of the lower boiling point components thus produced (the amount of the components having 10 or less carbon atoms) was 255 mg, while the amount of polyethylene thus produced was 22 mg. The catalytic activity calculated from the sum of these amounts of the products was 2770 g-product/(mmol-Cr·hr). Regarding the lower boiling point components, the selection rate of 1-hexene was 7.1% by mass, the selection rate of 1-octene was 90.9% by mass, and the catalytic activity of 1-octene was 2318 g-product/(mmol-Cr·hr). The results are shown in Table 1.

Examples 2 to 11

The reaction was carried out in the same manner as in Example 1, except that amine compounds (B-2) to (B-11) were used instead of the amine compound (B-1), respectively. The results are shown in Table 1.

TABLE 1

| | Amine compound (B) | Amount of α-olefine generated 1) (mg) | Amount of polyethylene generated 2) (mg) | Activity (g-product/ mmol-Cr · hr) | α-Olefine distribution (% by mass) | | Activity for 1-octene (g-product/ mmol-Cr · hr) |
|---|---|---|---|---|---|---|---|
| | | | | | 1-Hexene | 1-Octene | |
| Example 1 | B-1 | 255 | 22 | 2770 | 7.1 | 90.9 | 2318 |
| Example 2 | B-2 | 1164 | 100 | 12640 | 5.8 | 93.3 | 10860 |
| Example 3 | B-3 | 1151 | 3 | 11540 | 46.7 | 53.3 | 6135 |
| Example 4 | B-4 | 953 | 7 | 9600 | 39.0 | 61.0 | 5813 |
| Example 5 | B-5 | 279 | 1 | 2800 | 42.3 | 57.7 | 1610 |
| Example 6 | B-6 | 1274 | 10 | 12840 | 54.7 | 45.3 | 5771 |
| Example 7 | B-7 | 1188 | 20 | 12080 | 59.3 | 40.7 | 4835 |
| Example 8 | B-8 | 542 | 8 | 5500 | 73.6 | 26.4 | 1431 |
| Example 9 | B-9 | 1335 | 10 | 13450 | 59.6 | 40.4 | 5398 |
| Example 10 | B-10 | 1304 | 16 | 13200 | 28.0 | 71.8 | 9363 |
| Example 11 | B-11 | 201 | 16 | 2170 | 13.3 | 83.2 | 1672 |

1) Amount of components generated having 10 or less than 10 carbon atoms, i.e., components having lower boiling points.
2) Amount of polyethylene generated including components having 11 or greater than 11 carbon atoms, i.e., components having higher boiling points.

Comparative Examples 1 to 3

The reaction was carried out in the same manner as in Example 1, except that compounds (O-1), (O-2) and (P-1) represented by the following formulae (O-1), (O-2) and (P-1) (each compound was prepared by purifying the corresponding commercially available product by conventional methods) were used instead of the amine compound (B-1). The results are shown in Table 2.

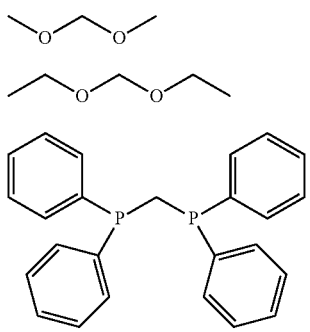

(O-1)

(O-2)

(P-1)

(2.5 MPa-G). Under the same pressure, the mixture was reacted at 60° C. for 60 minutes while ethylene was supplied. A small amount of isopropanol was added thereto to stop the reaction. After completion of the reaction, the reaction liquid was washed with 0.1 N aqueous solution of hydrochloric acid and pure water, and lower boiling point components (components having 10 or less carbon atoms) were separated from higher boiling point components and polyethylene by a liquid nitrogen trap under reduced pressure. The resultant products were analyzed by gas chromatography. The amount of lower boiling point components thus produced (the amount of the components having 10 or less carbon atoms) was 25700 mg, while the amount of polyethylene thus produced was 2000 mg. The catalytic activity calculated from the sum of these amounts of the products was 55400 g-product/(mmol-Cr·hr). Regarding the lower boiling point components, the selection rate of 1-hexene was 28.8% by mass, the selection rate of 1-octene was 67.5% by mass, and the catalytic activity of 1-octene was 34695 g-product/(mmol-Cr·hr). The results are shown in Table 3.

Example 13

The reaction was carried out in the same manner as in Example 12, except that an amine compound (B-10) was

TABLE 2

|  | Compound | Amount of α-olefine production 1) (mg) | Amount of polyethylene production 2) (mg) | Activity (g-product/ mmol-Cr · hr) | α-Olefine distribution (% by mass) | | Activity for 1-octene (g-product/ mmol-Cr · hr) |
|---|---|---|---|---|---|---|---|
|  |  |  |  |  | 1-Hexene | 1-Octene |  |
| Comparative example 1 | O-1 | 0.4 | 2.4 | 28 | 57.9 | 42.1 | 2 |
| Comparative example 2 | O-2 | 0.5 | 1.0 | 15 | 72.3 | 27.7 | 1 |
| Comparative example 3 | P-1 | 2.9 | 1.8 | 47 | 59.7 | 40.3 | 12 |

1) Amount of components generated having 10 or less than 10 carbon atoms, i.e., components having lower boiling points.
2) Amount of polyethylene generated including components having 11 or greater than 11 carbon atoms, i.e., components having higher boiling points.

Example 12

In an enoughly dried 100 mL Schlenk flask, 0.22 g (1.39 mmol) of an amine compound (B-6), 0.49 g (1.31 mmol) of chromium trichloride tristetrahydrofuran and 24 mL of dichloromethane were prepared and stirred for 20 hours under an argon atmosphere. After the reaction liquid was condensed to about ½ under reduced pressure, 15 mL of n-hexane was added thereto. The mixture was stirred for a while, and condensed to about ⅔ under reduced pressure. The insoluble component was collected by filtration through a glass filter. After the insoluble component was washed with 20 mL of n-hexane, the product was dried under reduced pressure, to obtain 0.26 g of a chromium compound. As a result of analysis, the chromium concentration was 16.5% by mass. Methylcyclohexane was added to this chromium compound, to prepared a methylcyclohexane solution (catalyst solution) at the concentration of 0.001 mmol/mL as a converted value based on the number of chromium atoms.

In a fully nitrogen-purged autoclave having an internal volume of 500 mL, methylaluminoxane (Tosoh Finechem Corporation MMAO-3A, 5.7% by mass hexane solution) was added to 148 mL of methylcyclohexane, in an amount of 2.5 mmol as a converted value based on the number of aluminum atoms. Subsequently, 0.50 mL (0.0005 mmol) of the catalyst solution previously prepared was added thereto, and the reaction was started under the pressure by ethylene used instead of the amine compound (B-6). The amount of lower boiling point components thus produced (the amount of α-olefins having 10 or less carbon atoms) was 17200 mg, while the amount of polyethylene thus produced was 1400 mg. The catalytic activity calculated from the sum of these amounts of the products was 37200 g-product/(mmol-Cr·hr). Regarding the lower boiling point components, the selection rate of 1-hexene was 15.3% by mass, the selection rate of 1-octene was 82.4% by mass, and the catalytic activity of 1-octene was 28346 g-product/(mmol-Cr·hr). The results are shown in Table 3.

Example 14

The reaction was carried out in the same manner as in Example 13, except that the reaction temperature was changed from 60° C. to 70° C. The amount of lower boiling point components thus produced was 24300 mg, the amount of polyethylene thus produced was 1200 mg. The catalytic activity calculated from the sum of these amounts of the products was 51000 g-product/(mmol-Cr·hr). Regarding the lower boiling point components, the selection rate of 1-hexene was 22.6% by mass, the selection rate of 1-octene was 74.9% by mass, and the catalytic activity of 1-octene was 36401 g-product/(mmol-Cr·hr). The results are shown in Table 3.

TABLE 3

| | Amine compound (B) | Amount of α-olefine production 1) (mg) | Amount of polyethylene production 2) (mg) | Activity (g-product/ mmol-Cr · hr) | α-Olefine distrbution (% by mass) | | Activity for 1-octene (g-product/ mmol-Cr · hr) |
|---|---|---|---|---|---|---|---|
| | | | | | 1-Hexene | 1-Octene | |
| Example 12 | B-6 | 25,700 | 2,000 | 55400 | 28.8 | 67.5 | 34695 |
| Example 13 | B-10 | 17,200 | 1,400 | 37200 | 15.3 | 82.4 | 28346 |
| Example 14 (70° C.) | B-10 | 24,300 | 1,200 | 51000 | 22.6 | 74.9 | 36401 |

1) Amount of components generated having 10 or less than 10 carbon atoms, i.e., components having lower boiling points.
2) Amount of polyethylene generated including components having 11 or greater than 11 carbon atoms, i.e., components having higher boiling points.

INDUSTRIAL APPLICABILITY

The olefin oligomerization catalyst of the present invention has an excellent activity, and particularly, provides a high selectivity and a production efficiency of olefin oligomers such as 1-octene, and is extremely useful for production of olefin oligomers. Therefore, the present invention has an industrially extremely high value.

The invention claimed is:

1. A method for producing an olefin oligomer, comprising performing an olefin oligomerization reaction in the presence of an olefin oligomerization catalyst containing the following components (A) to (C):
(A) a chromium compound,
(B) an amine compound represented by the following general formula (1):

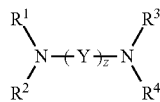

(in the general formula (1), $R^1$ to $R^4$ may be the same or different from each other, and each represents a hydrogen atom, a halogen atom, a hydrocarbon group that does not contain a nitrogen-containing group or a phosphorus-containing group, a heterocyclic compound residue, an oxygen-containing group, a boron-containing group, an aluminum-containing group, a sulfur-containing group, a silicon-containing group, a germanium-containing group or a tin-containing group, and two or more thereof may be connected each other, Y represents a carbon atom having substituents $R^5$ and $R^6$ (a structure represented by —$CR^5R^6$—), $R^5$ and $R^6$ may be the same or different from each other, and each represents a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and $R^5$ and $R^6$ may be connected each other, and each of $R^5$ and $R^6$ may be connected to any one of $R^1$ to $R^4$,
Z represents an integer of 1 to 10) and
(C) at least one compound selected from the group consisting of
(C-1) an organometal compound,
(C-2) an organoaluminumoxy compound and
(C-3) a compound reacting with a transition metal compound to form an ion pair.

2. The method for producing an olefin oligomer according to claim 1, wherein an amine compound (B) represented by the general formula (1) is used, in which $R^1$ is not connected to $R^3$ and $R^4$, and $R^2$ is not connected to $R^3$ and $R^4$.

3. The method for producing an olefin oligomer according to claim 1, wherein an amine compound (B) represented by the general formula (1) is used, in which Z is an integer of 1 to 3.

4. The method for producing an olefin oligomer according to claim 1, wherein an amine compound (B) represented by the general formula (1) is used, in which Z is 1.

5. The method for producing an olefin oligomer according to claim 1, wherein an amine compound (B) represented by the general formula (1) is used, in which Z is an integer of 2 to 10.

6. The method for producing an olefin oligomer according to claim 1, wherein the catalyst contains the following component (D) in addition to the components (A) to (C):
(D) a carrier for carrying at least one compound selected from the group consisting of the components (A) to (C).

7. The method for producing an olefin oligomer according to claim 1, wherein the olefin oligomerization reaction is performed in the presence of an antistatic agent.

8. The method for producing an olefin oligomer according to claim 1, wherein the olefin is ethylene.

9. The method for producing an olefin oligomer according to claim 1, wherein the olefin oligomer is 1-octene.

10. The method for producing an olefin oligomer according to claim 1, wherein in the general formula (1), $R^1$ to $R^4$ may be the same or different from each other, and each represents a hydrogen atom, a halogen atom, a hydrocarbon group, a heterocyclic compound residue, an oxygen-containing group, a boron-containing group, an aluminum-containing group, a sulfur-containing group, a silicon-containing group, a germanium-containing group or a tin-containing group, and two or more thereof may be connected each other, and
Y represents a carbon atom having substituents $R^5$ and $R^6$ (a structure represented by —$CR^5R^6$—), $R^5$ and $R^6$ may be the same or different from each other, and each represents a hydrogen atom, a halogen atom, a hydrocarbon group, a heterocyclic compound residue, an oxygen-containing group, a boron-containing group, an aluminum-containing group, a sulfur-containing group, a phosphorus-containing group, a silicon-containing group, a germanium-containing group or a tin-containing group, and $R^5$ and $R^6$ may be connected each other, and each of R5 and R6 may be connected to any one of $R^1$ to R4.

11. The method for producing an olefin oligomer according to claim 1, wherein the chromium compound (A) contains a halogen atom.

12. The method for producing an olefin oligomer according to claim 1, wherein the heterocyclic compound residue is without the one which contains a nitrogen and phosphorus atom.

* * * * *